(12) United States Patent
Cashman

(10) Patent No.: US 8,778,958 B2
(45) Date of Patent: *Jul. 15, 2014

(54) SYNTHESIS OF METABOLICALLY STABLE AGENTS FOR ALCOHOL AND DRUG ABUSE

(76) Inventor: John R. Cashman, San Diego, CA (US)

( * ) Notice: Subject to any disclaimer, the term of this patent is extended or adjusted under 35 U.S.C. 154(b) by 447 days.

This patent is subject to a terminal disclaimer.

(21) Appl. No.: 13/003,564

(22) PCT Filed: Jul. 9, 2009

(86) PCT No.: PCT/US2009/050041
§ 371 (c)(1),
(2), (4) Date: Mar. 7, 2011

(87) PCT Pub. No.: WO2010/006119
PCT Pub. Date: Jan. 14, 2010

(65) Prior Publication Data
US 2011/0263630 A1  Oct. 27, 2011

Related U.S. Application Data

(60) Provisional application No. 61/134,699, filed on Jul. 10, 2008, provisional application No. 61/209,615, filed on Mar. 9, 2009.

(51) Int. Cl.
*A61K 31/485* (2006.01)
*C07D 489/08* (2006.01)

(52) U.S. Cl.
USPC ............................... 514/282; 546/44; 546/46

(58) Field of Classification Search
USPC ...................................... 514/282; 546/44, 45
See application file for complete search history.

(56) References Cited

U.S. PATENT DOCUMENTS 6,177,438 B1  1/2001  Nagase et al.

FOREIGN PATENT DOCUMENTS

| EP | 1762569 A1 | 3/2007 |
| EP | 1810973 A1 | 7/2007 |
| WO | 2005117589 A1 | 12/2005 |

OTHER PUBLICATIONS

Sayre, L. M. et al.: Design and synthesis of naltrexone-deriived affinity labels with nonequilibrium opioid agonist and antagonist activities. Evidence for the existance of different mu receptor subtypes in different tissues. J. Med. Chem., vol. 27, pp. 1325-1335, 1984.*
Langer, New Methods of Drug Delivery. Science, Sep. 28, 1990; 249(4976):1527-1533.
Wee et al., Effects of Dose and Session Duration on Cocaine Self-Administration in Rats. J Pharmacol Exp Ther, Mar. 2007;320(3):1134-1143.
Extended European Search Report as reported in EP 09795163.6 dated Nov. 24, 2011.
ISR and WO as reported in PCT/US2009/050041 dated Aug. 24, 2009.
Derrick et al., 6n-Cinnamoyl-Beta-Naltrexamine and Its P-Nitro Derivative. High Efficacy K-Opioid Agonjsts With Weak Antagonist Actions. Biorganic & Medicinal Chemistry Letters, 1996;6(2):167-172.
Ghirmai et al., Synthesis and Biological Evaluation of a.- and P-6-Amido Derivatives of 17-Cyclopropylmethyl-3, 14P-dihydroxy-4, Sa.-epoxymorphinan: Potential Alcohol-Cessation Agents. J. Med. Chem. 2008;51:1913-1924.
Metcalf and Coop, Kappa Opioid Antagonists: Past Successess and Future Prospects. The AAPS Journal 2005; 7 (3) Article 71:E704-E722.
Mohamed et al., Activity of N -Methyl-alpha- and -beta-funaltrexamine at Opioid Receptors. J. Med. Chem. 1986;29:1551-1653.
Nagase et al., Discovery of a Structurally Novel Opioid K-Agonist Derived From 4,5-Epoxymorphinan. Chem. Pharm. Bull. 1998; 46(2):366-369.
Ohno et al., Solid-Phase Synthesis of 6-Sulfonylamino Morphinan Libraries. Synlett, 2002; 1:93-96.
Pogozheva et al., Homology Modeling of Opioid Receptor-Ligand Complexes Using Experimental Constraints. The AAPS Journal 2005; 7 (2) Article 43:E434-E448.
Portoghese et al., Persistent Binding of Fatty Acyl Derivatives of Naltrexamine to Opioid Receptors. Journal of Medicinal Chemistry, 1991;34(7):1966-1969.

* cited by examiner

*Primary Examiner* — Charanjit Aulakh

(57) ABSTRACT

The disclosed opioid-related compounds and pharmaceutical compositions thereof, are useful in a variety of applications relating to the modulation of receptors and receptor signaling within and outside the nervous system. For example, the compounds and compositions are useful in methods for the treatment of addictions and other CNS-related disorders. The disclosed compounds can be delivered or administered to a mammal including humans, alone in the form of a pharmaceutically acceptable salt or hydrolysable precursor thereof, or in the form of a pharmaceutical composition, wherein a therapeutically effective amount of a compound is mixed with suitable carriers or excipients.

11 Claims, 1 Drawing Sheet

SYNTHESIS OF METABOLICALLY STABLE AGENTS FOR ALCOHOL AND DRUG ABUSE

RELATED APPLICATIONS

The present application is filed under 35 U.S.C. §371 as the U.S. national phase of International Application PCT/US2009/050041 filed Jul. 9, 2009, which designated the U.S. and claims priority to U.S. Provisional Patent Application No. 61/134,699, filed Jul. 10, 2008, and U.S. Provisional Patent Application No. 61/209,615, filed Mar. 7, 2009. The entire disclosure of all of the above applications are incorporated by reference herein.

FIELD OF THE INVENTION

The present invention is in the field of pharmaceutical agents for the cessation of alcohol, tobacco and drug addiction and abuse.

BACKGROUND OF THE DISCLOSURE

Dependence on alcohol, tobacco and illicit drug abuse is a serious worldwide public health issue with significant social and economic consequences. Drug and alcohol addiction is characterized by compulsive intake and withdrawal symptoms such as craving, depression and dysphoria (American Psychiatric Association, 2000). It has been hypothesized that the emergence of a negative emotional state during drug withdrawal not only provides a key marker for the development of dependence but may also be etiological for compulsive alcohol and drug taking associated with addiction. Such negative emotional states can contribute to relapse, and one of the most frequent determinants of relapse is reported to be a negative emotional state in alcoholism, heroin addiction and binge eating disorder. Therefore, adaptations in neurotransmitter systems that are involved in negative emotional states may underlie the development of drug addiction.

In 1994, naltrexone was approved by the United States FDA for the treatment of alcoholism. Naltrexone, along with acamprosate and disulfuram are the only agents currently available to treat alcohol dependence. In a number of clinical studies naltrexone has shown benefit for treating alcoholism in heavy drinkers, and moderate to severe alcoholism. However, naltrexone is not successful in treating all alcoholics and adverse effects including intolerable nausea and hepatotoxicity confound treatment of patients with liver disease. It may be that metabolic bioactivation of naltrexone to a reactive metabolic intermediate contributes to the hepatotoxicity observed. Diminished effect over time, relatively low bioavailability and possibly relatively low affinity for δ and κ opioid receptors or genetic variability of the opioid receptors may explain the less than consistent efficacy of naltrexone. Nalmefene possesses superior pharmaceutical properties compared with naltrexone but also suffers from hepatotoxic side effects.

Studies using rodent animal models have shown that naltrexone decreases alcohol self-administration, suggesting that these types of agents may prevent the reinforcing effects of alcohol consumption. However, some opioid receptor antagonists decrease both ethanol and sucrose intake in rats. Certain opioid receptor agonists stimulate food consumption in preclinical animal models of obesity and opioid receptor antagonists inhibit energy-rich food consumption. It may be that opioid receptor antagonists prevent central reward mechanisms that share common neural substrates responsible for the development of alcohol dependence.

Opioid receptors are well-characterized receptors and numerous studies suggest that alcohol and illicit drugs interacts with endogenous opioid systems (e.g., naltrexone is a pure opioid μ receptor antagonist with no agonist activity and no abuse potential). Antagonizing opioid receptors decrease the effects of alcohol and drug-mediated pleasure-inducing endogenous opioids. By attenuating the positive reinforcing effects of alcohol consumption, opioid receptor antagonists have direct effects on alcohol and drug-seeking behavior. A decrease in alcohol and drug consumption by antagonism of opioid receptors suggests direct effects on this reinforcement system and animal studies have shown that μ, δ- and κ-opioid receptors contribute to alcohol and drug-induced reinforcement.

SUMMARY OF THE INVENTION

In one embodiment, disclosed herein are compounds having pharmacological activity as treatments for addiction and substance abuse.

In a typical embodiment, the compounds disclosed herein are used to treat addiction to alcohol and other stimulants, such as nicotine or cocaine.

In another embodiment, the compounds inhibit the self-administration of alcohol, cocaine and other substances of abuse.

In another embodiment, the compounds disclosed herein have functional activity against opioid receptors.

In yet another embodiment, the compounds have activity as antagonists, partial antagonists, partial agonists, inverse agonists or partial inverse agonists of the mu (μ), delta (δ) and kappa (κ) opioid receptors.

In another embodiment, the compounds disclosed herein are used to decrease consumption of alcohol.

In another embodiment, the compounds disclosed herein are used to decrease consumption of cocaine or tobacco.

In another embodiment, disclosed herein are compounds of Formula I:

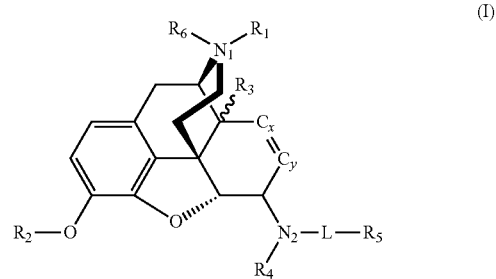

(I)

or a pharmaceutically acceptable salt thereof,
where
$R_1$ is selected from the group consisting of hydrogen, optionally substituted alkyl, optionally substituted alkenyl, optionally substituted alkynyl, optionally substituted cycloalkyl, optionally substituted cycloalkenyl, optionally substituted aryl, and optionally substituted heteroaryl;
$R_2$ is selected from the group consisting of hydrogen, optionally substituted alkyl, optionally substituted alkenyl, optionally substituted optionally substituted alkynyl, and optionally substituted akanoyl;
$R_3$ is selected from the group consisting of hydrogen, OH, and optionally substituted alkoxy;

$R_4$ is selected from the group consisting of hydrogen, optionally substituted alkyl, optionally substituted alkenyl, optionally substituted alkynyl, optionally substituted cycloalkyl, optionally substituted cycloalkenyl, optionally substituted aryl, and optionally substituted heteroaryl;

L is a group linking $N_2$ and $R_5$ consisting of a bond, $CH_2$, C=O, S(=O)$_2$, (C=O)—NH—, and (C=O)—O—;

$R_5$ is selected from the group consisting of hydrogen, optionally substituted alkyl, optionally substituted alkenyl, optionally substituted alkynyl, optionally substituted cycloalkyl, optionally substituted cycloalkenyl, optionally substituted aryl, and optionally substituted heteroaryl;

$R_6$ is selected from the group consisting of hydrogen, O$^-$, $CH_3$, and optionally substituted alkoxy, or $R_6$ is absent;

$N_1$ is a nitrogen atom, which is neutral when $R_6$ is absent, or is charged when $R_6$ is present, to satisfy the normal valence of a tertiary or quaternary nitrogen;

$N_2$ is a nitrogen atom, which is bound to the opiate nucleus in α or β stereochemistry or a mixture thereof; and $C_x$ and $C_y$ together form an alkylidene group (—$CH_2$—$CH_2$—) or alkenylidene group (—CH=CH—); any of the attached hydrogens may be replaced to form a substituted alkenylidene group or substituted alkylidene of any possible stereochemistry.

DETAILED DESCRIPTION OF THE EMBODIMENTS

Figure 1:
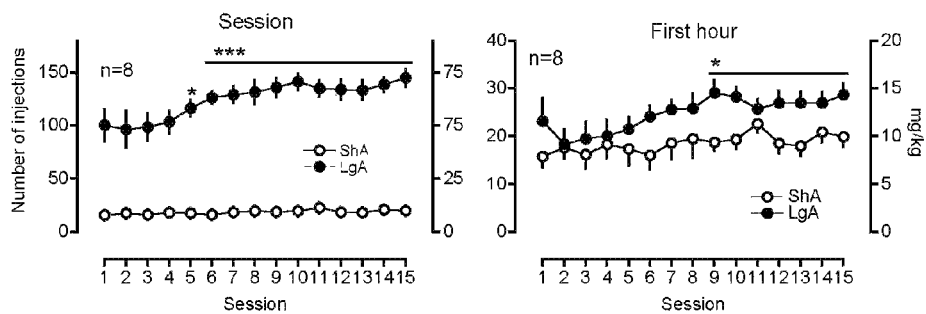
FIG. 1 shows graphs depicting the results of cocaine self-administration under a fixed-ratio schedule of reinforcement.

In one embodiment the opioid-related compounds disclosed herein are useful in a variety of applications relating to the modulation of receptors and receptor signaling within and outside the nervous system. Disclosed herein are also pharmaceutical compositions and methods for the treatment of addictions and other CNS-related disorders. The agents disclosed herein can be delivered or administered to a mammal (e.g., human subject), alone in the form of a pharmaceutically acceptable salt or hydrolysable precursor thereof or in the form of a pharmaceutical composition wherein the compound is mixed with suitable carriers or excipients in a therapeutically effective amount.

DEFINITIONS

Unless defined otherwise, all technical and scientific terms used herein have the same meaning as commonly understood by one of ordinary skill in the art to which this invention belongs. Although any methods and material similar to those described herein can be used in the practice or testing of the present invention, only examples of methods and materials are described. For purposes of the present invention, the following terms are defined below.

The terms "a," "an," and "the" include plural referents unless the context clearly dictates otherwise.

Specific values listed below for radicals, substituents, and ranges are for illustration only, they do not exclude other defined values or other values within defined ranges for the radicals and substituents.

"Substituted" or "optionally substituted" is intended to indicate that one or more hydrogens on the atom indicated in the expression using "substituted" is replaced with a selection from the indicated group(s), provided that the indicated atom's normal valency is not exceeded, and that the substitution results in a stable compound. Suitable indicated groups include, e.g., alkyl, alkenyl, alkylidenyl, alkenylidenyl, alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, $NR_xR_y$ and/or $COOR_x$, wherein each $R_x$ and $R_y$ are independently H, alkyl, alkenyl, aryl, heteroaryl, heterocycle, cycloalkyl or hydroxy, or wherein $R_x$ and $R_y$, taken together along with the nitrogen atom to which they are attached form a heterocycle ring. When a substituent is keto (i.e., =O) or thioxo (i.e., =S) group, then 2 hydrogens on the atom are replaced.

"Alkyl" refers to a C1-C18 hydrocarbon containing normal, secondary, tertiary or cyclic carbon atoms. Examples are methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —CH($CH_3$)$_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —CH($CH_3$)$CH_2CH_3$), 2-methyl-2-propyl (t-Bu, t-butyl, —C($CH_3$)$_3$), pentyl (n-pentyl, —$CH_2CH_2CH_2CH_2CH_3$), 2-pentyl (—CH($CH_3$)$CH_2CH_2CH_3$), 3-pentyl (—CH($CH_2CH_3$)$_2$), 2-methyl-2-butyl (—C($CH_3$)$_2CH_2CH_3$), 3-methyl-2-butyl (—CH($CH_3$)CH($CH_3$)$_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—CH($CH_3$)$CH_2CH_2CH_2CH_3$), 3-hexyl (—CH($CH_2CH_3$)($CH_2CH_2CH_3$)), 2-methyl-2-pentyl (—C($CH_3$)$_2CH_2CH_2CH_3$), 3-methyl-2-pentyl (—CH($CH_3$)CH($CH_3$)$CH_2CH_3$), 4-methyl-2-pentyl (—CH($CH_3$)$CH_2CH(CH_3)_2$), 3-methyl-3-pentyl (—C($CH_3$)($CH_2CH_3$)$_2$), 2-methyl-3-pentyl (—CH($CH_2CH_3$)CH($CH_3$)$_2$), 2,3-dimethyl-2-butyl (—C($CH_3$)$_2$CH($CH_3$)$_2$), 3,3-dimethyl-2-butyl (—CH($CH_3$)C($CH_3$)$_3$.

The alkyl can optionally be substituted with one or more alkenyl, alkylidenyl, alkenylidenyl, alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, $NR_xR_y$ and/or $COOR_x$, wherein each $R_x$ and $R_y$ are independently H, alkyl, alkenyl, aryl, heteroaryl, heterocycle, cycloalkyl or hydroxyl, or wherein $R_x$ and $R_y$, taken together along with the nitrogen atom to which they are attached form a heterocycle ring. The alkyl can optionally be interrupted with one or more non-peroxide oxy (—O—), thio (—S—), carbonyl (—C(=O)—), carboxy (—C(=O)O—), sulfonyl (SO) or sulfoxide (SO$_2$). Additionally, the alkyl can optionally be at least partially unsaturated, thereby providing an alkenyl.

"Alkenyl" refers to a $C_2$-$C_{18}$ hydrocarbon containing normal, secondary, tertiary or cyclic carbon atoms with at least one site of unsaturation, i.e., a carbon-carbon, sp$^2$ double bond. Examples include, but are not limited to: ethylene or vinyl (—CH=$CH_2$), allyl (—$CH_2$CH=$CH_2$), cyclopentenyl (—$C_5H_7$), and 5-hexenyl (—$CH_2CH_2CH_2CH_2$CH=$CH_2$).

The alkenyl can optionally be substituted with one or more alkyl, alkylidenyl, alkenylidenyl, alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, $NR_xR_y$ and/or $COOR_x$, wherein each $R_x$ and $R_y$ are independently H, alkyl, alkenyl, aryl, heteroaryl, heterocycle, cycloalkyl or hydroxyl, or wherein $R_x$ and $R_y$, taken together along with the nitrogen atom to which they are attached form a heterocycle ring. Additionally, the alkenyl can optionally be interrupted with one or more peroxide oxy (—O—), thio (—S—), carbonyl (—C(=O)—), carboxy (—C(=O)O—), sulfonyl (SO) or sulfoxide ($SO_2$).

"Alkylidenyl" refers to a $C_1$-$C_{18}$ hydrocarbon containing normal, secondary, tertiary or cyclic carbon atoms. Examples are methylidenyl (=$CH_2$), ethylidenyl (=$CHCH_3$), 1-propylidenyl (=$CHCH_2CH_3$), 2-propylidenyl (=$C(CH_3)_2$), 1-butylidenyl (=$CHCH_2CH_2CH_3$), 2-methyl-1-propylidenyl (=$CHCH(CH_3)_2$), 2-butylidenyl (=$C(CH_3)CH_2CH_3$), 1-pentylidenyl (=$CHCH_2CH_2CH_2CH_3$), 2-pentylidenyl (=$C(CH_3)CH_2CH_2CH_3$), 3-pentylidenyl (=$C(CH_2CH_3)_2$), 3-methyl-2-butylidenyl (=$C(CH_3)CH(CH_3)_2$), 3-methyl-1-butylidenyl (=$CHCH_2CH(CH_3)_2$), 2-methyl-1-butylidenyl (=$CHCH(CH_3)CH_2CH_3$), 1-hexylidenyl (=$CHCH_2CH_2CH_2CH_2CH_3$), 2-hexylidenyl (=$C(CH_3)CH_2CH_2CH_2CH_3$), 3-hexylidenyl (=$C(CH_2CH_3)(CH_2CH_2CH_3)$), 3-methyl-2-pentylidenyl (=$C(CH_3)CH(CH_3)CH_2CH_3$), 4-methyl-2-pentylidenyl (=$C(CH_3)CH_2CH(CH_3)_2$), 2-methyl-3-pentylidenyl (=$C(CH_2CH_3)CH(CH_3)_2$), and 3,3-dimethyl-2-butylidenyl (=$C(CH_3)C(CH_3)_3$).

The alkylidenyl can optionally be substituted with one or more alkyl, alkenyl, alkenylidenyl, alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, $NR_xR_y$ and/or $COOR_x$, wherein each $R_x$ and $R_y$ are independently H, alkyl, alkenyl, aryl, heteroaryl, heterocycle, cycloalkyl or hydroxyl, or wherein $R_x$ and $R_y$, taken together along with the nitrogen atom to which they are attached form a heterocycle ring. Additionally, the alkylidenyl can optionally be interrupted with one or more non-peroxide oxy (—O—), thio (—S—), carbonyl (—C(=O)—), carboxy (—C(=O)O—), sulfonyl (SO) or sulfoxide ($SO_2$).

"Alkenylidenyl" refers to a $C_2$-$C_{20}$ hydrocarbon containing normal, secondary, tertiary or cyclic carbon atoms with at least one site of unsaturation, i.e., a carbon-carbon, $sp^2$ double bond. Examples include, but are not limited to: allylidenyl (=CHCH=$CH_2$), and 5-hexenylidenyl (=$CHCH_2CH_2CH_2CH$=$CH_2$).

The alkenylidenyl can optionally be substituted with one or more alkyl, alkenyl, alkylidenyl, alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, $NR_xR_y$ and/or $COOR_x$, wherein each $R_x$ and $R_y$ are independently H, alkyl, alkenyl, aryl, heteroaryl, heterocycle, cycloalkyl or hydroxyl, or wherein $R_x$ and $R_y$, taken together along with the nitrogen atom to which they are attached form a heterocycle ring. Additionally, the alkenylidenyl can optionally be interrupted with one or more non-peroxide oxy (—O—), thio (—S—), carbonyl (—C(=O)—), carboxy (—C(=O)O—), sulfonyl (SO) or sulfoxide ($SO_2$).

"Alkylene" refers to a saturated, branched or straight chain or cyclic hydrocarbon radical of 1-18 carbon atoms, and having two monovalent radical centers derived by the removal of two hydrogen atoms from the same or different carbon atoms of a parent alkane. Typical alkylene radicals include, but are not limited to: methylene (—$CH_2$—), 1,2-ethyl (—$CH_2CH_2$—), 1,3-propyl (—$CH_2CH_2CH_2$—), 1,4-butyl (—$CH_2CH_2CH_2CH_2$—), and the like.

The alkylene can optionally be substituted with one or more alkyl, alkenyl, alkylidenyl, alkenylidenyl, alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, $NR_xR_y$ and/or $COOR_x$, wherein each $R_x$ and $R_y$ are independently H, alkyl, alkenyl, aryl, heteroaryl, heterocycle, cycloalkyl or hydroxyl, or wherein $R_x$ and $R_y$, taken together along with the nitrogen atom to which they are attached form a heterocycle ring. Additionally, the alkylene can optionally be interrupted with one or more nonperoxide oxy (—O—), thio (—S—), carbonyl (—C(=O)—), carboxy (—C(=O)O—), sulfonyl (SO) or sulfoxide ($SO_2$). Moreover, the alkylene can optionally be at least partially unsaturated, thereby providing an alkenylene.

"Alkenylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkene. Typical alkenylene radicals include, but are not limited to: 1,2-ethylene (—CH=CH—).

The alkenylene can optionally be substituted with one or more alkyl, alkenyl, alkylidenyl, alkenylidenyl, alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, $NR_xR_y$ and/or $COOR_x$, wherein each $R_x$ and $R_y$ are independently H, alkyl, alkenyl, aryl, heteroaryl, heterocycle, cycloalkyl or hydroxyl, or wherein $R_x$ and $R_y$, taken together along with the nitrogen atom to which they are attached form a heterocycle ring. Additionally, The alkenylene can optionally be interrupted with one or more non-peroxide oxy (—O—), thio (—S—), carbonyl (—C(=O)—), carboxy (—C(=O)O—), sulfonyl (SO) or sulfoxide ($SO_2$).

The term "alkynyl" refers to unsaturated groups which contain at least one carbon-carbon triple bond and includes straight chain, branched chain, and cyclic groups, all of which may be optionally substituted. Suitable alkynyl groups include ethynyl, propynyl, butynyl and the like which may be optionally substituted.

The term "alkoxy" refers to the groups alkyl-O—, where alkyl is defined herein. Preferred alkoxy groups include, e.g., methoxy, ethoxy, n-propoxy, iso-propoxy, n-butoxy, tert-butoxy, sec-butoxy, n-pentoxy, n-hexoxy, 1,2-dimethylbutoxy, and the like.

The alkoxy can optionally be substituted with one or more alkyl, alkylidenyl, alkenylidenyl, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, $NR_xR_y$ and $COOR_x$, wherein each $R_x$ and $R_y$ are independently H, alkyl, aryl, heteroaryl, heterocycle, cycloalkyl or hydroxyl, or wherein $R_x$ and $R_y$, taken together along with the nitrogen atom to which they are attached form a heterocycle ring.

The term "aryl" refers to an unsaturated aromatic carbocyclic group of from 6 to 20 carbon atoms having a single ring (e.g., phenyl) or multiple condensed (fused) rings, wherein at least one ring is aromatic (e.g., naphthyl, dihydrophenanthrenyl, fluorenyl, or anthryl). Preferred aryls include phenyl, naphthyl and the like.

The aryl can optionally be substituted with one or more alkyl, alkenyl, alkoxy, halo, haloalkyl, hydroxy, hydroxyalkyl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, $NR_xR_y$ and $COOR_x$, wherein each $R_x$ and $R_y$ are independently H, alkyl, aryl, heteroaryl, heterocycle, cycloalkyl or hydroxyl, or wherein $R_x$ and $R_y$, taken together along with the nitrogen atom to which they are attached form a heterocycle ring.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and the like.

The cycloalkyl can optionally be substituted with one or more alkyl, alkenyl, alkoxy, halo, haloalkyl, hydroxy, hydroxyalkyl, aryl, heteroaryl, heterocycle, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, $NR_xR_y$ and $COOR_x$, wherein each $R_x$ and $R_y$ are independently H, alkyl, aryl, heteroaryl, heterocycle, cycloalkyl or hydroxyl, or wherein $R_x$ and $R_y$, taken together along with the nitrogen atom to which they are attached form a heterocycle ring.

The cycloalkyl can optionally be at least partially unsaturated, thereby providing a cycloalkenyl.

The term "halo" refers to fluoro, chloro, bromo, and iodo. Similarly, the term "halogen" refers to fluorine, chlorine, bromine, and iodine.

"Haloalkyl" refers to alkyl as defined herein substituted by 1-4 halo groups as defined herein, which may be the same or different. Representative haloalkyl groups include, by way of example, trifluoromethyl, 3-fluorododecyl, 12,12,12-trifluorododecyl, 2-bromooctyl, 3-bromo-6-chloroheptyl, and the like.

The term "heteroaryl" is defined herein as a monocyclic, bicyclic, or tricyclic ring system containing one, two, or three aromatic rings and containing at least one nitrogen, oxygen, or sulfur atom in an aromatic ring, and which can be unsubstituted or substituted, for example, with one or more, and in particular one to three, substituents, like halo, alkyl, hydroxy, hydroxyalkyl, alkoxy, alkoxyalkyl, haloalkyl, nitro, amino, alkylamino, acylamino, alkylthio, alkylsulfinyl, and alkylsulfonyl. Examples of heteroaryl groups include, but are not limited to, 2H-pyrrolyl, 3H-indolyl, 4Hquinolizinyl, 4nH-carbazolyl, acridinyl, benzo[b]thienyl, benzothiazolyl, β-carbolinyl, carbazolyl, chromenyl, cinnaolinyl, dibenzo[b,d]furanyl, furazanyl, furyl, imidazolyl, imidizolyl, indazolyl, indolisinyl, indolyl, isobenzofuranyl, isoindolyl, isoquinolyl, isothiazolyl, isoxazolyl, naphthyridinyl, naptho[2,3-b], oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrimidinyl, pyrrolyl, quinazolinyl, quinolyl, quinoxalinyl, thiadiazolyl, thianthrenyl, thiazolyl, thienyl, triazolyl, and xanthenyl. In one embodiment the term "heteroaryl" denotes a monocyclic aromatic ring containing five or six ring atoms containing carbon and 1, 2, 3, or 4 heteroatoms independently selected from the group non-peroxide oxygen, sulfur, and N(Z) wherein Z is absent or is H, O, alkyl, phenyl or benzyl. In another embodiment heteroaryl denotes an ortho-bicyclic heterocycle of about eight to ten ring atoms derived therefrom, particularly a benz-derivative or one derived by fusing a propylene, or tetramethylene diradical thereto.

The heteroaryl can optionally be substituted with one or more alkyl, alkenyl, alkoxy, halo, haloalkyl, hydroxy, hydroxyalkyl, aryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, $NR_xR_y$ and $COOR_x$, wherein each $R_x$ and $R_y$ are independently H, alkyl, aryl, heteroaryl, heterocycle, cycloalkyl or hydroxyl, or wherein $R_x$ and $R_y$, taken together along with the nitrogen atom to which they are attached form a heterocycle ring.

The term "heterocycle" refers to a saturated or partially unsaturated ring system, containing at least one heteroatom selected from the group oxygen, nitrogen, and sulfur, and optionally substituted with alkyl or $C(=O)OR_b$, wherein $R_b$ is hydrogen or alkyl. Typically heterocycle is a monocyclic, bicyclic, or tricyclic group containing one or more heteroatoms selected from the group oxygen, nitrogen, and sulfur. A heterocycle group also can contain an oxo group (=O) attached to the ring. Non-limiting examples of heterocycle groups include 1,3-dihydrobenzofuran, 1,3-dioxolane, 1,4-dioxane, 1,4-dithiane, 2H-pyran, 2-pyrazoline, 4H-pyran, chromanyl, imidazolidinyl, imidazolinyl, indolinyl, isochromanyl, isoindolinyl, morpholine, piperazinyl, piperidine, piperidyl, pyrazolidine, pyrazolidinyl, pyrazolinyl, pyrrolidine, pyrroline, quinuclidine, and thiomorpholine.

The heterocycle can optionally be substituted with one or more alkyl, alkenyl, alkoxy, halo, haloalkyl, hydroxy, hydroxyalkyl, aryl, heteroaryl, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, $NR_xR_y$ and $COOR_x$, wherein each $R_x$ and $R_y$ are independently H, alkyl, aryl, heteroaryl, heterocycle, cycloalkyl or hydroxyl, or wherein $R_x$ and $R_y$, taken together along with the nitrogen atom to which they are attached form a heterocycle ring.

Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, morpholino, piperidinyl, tetrahydrofuranyl, and the like as well as N-alkoxy-nitrogen containing heterocycles. In one specific embodiment of the invention, the nitrogen heterocycle can be 3-methyl-5,6-dihydro-4H-pyrazino[3,2,1-jk]carbazol-3-ium iodide.

Another class of heterocyclics is known as "crown compounds" which refers to a specific class of heterocyclic compounds having one or more repeating units of the formula [—$(CH_2)_a$A-] where a is equal to or greater than 2, and A at each separate occurrence can be O, N, S or P. Examples of crown compounds include, by way of example only, [—$(CH_2)_3$—NH—$]_3$, [—$((CH_2)_2$—O$)_4$—$((CH_2)_2$—NH$)_2$] and the like. Typically such crown compounds can have from 4 to 10 heteroatoms and 8 to 40 carbon atoms.

The term "alkanoyl" refers to C(=O)R, wherein R is an alkyl group as previously defined.

The term "substituted alkanoyl" refers to C(=O)R, wherein R is a substituted alkyl group as previously defined.

The term "acyl" refers to C(=O)R, wherein R is an optionally substituted alkyl, optionally substituted cycloalkyl, optionally substituted aryl, optionally substituted heteroaryl, optionally substituted heterocyclyl group as previously defined. Examples of acyl groups include, but are not limited to acetyl, benzoyl, cyclohexanecarbonyl, nicotinoyl, and the like.

The term "acyloxy" refers to —O—C(=O)R, wherein R is an alkyl group as previously defined. Examples of acyloxy groups include, but are not limited to, acetoxy, propanoyloxy, butanoyloxy, and pentanoyloxy. Any alkyl group as defined above can be used to form an acyloxy group.

The term "alkoxycarbonyl" refers to C(=O)OR, wherein R is an alkyl group as previously defined.

The term "amino" refers to —NH$_2$, and the term "alkylamino" refers to —NR$_2$, wherein at least one R is alkyl and the second R is alkyl or hydrogen. The term "acylamino" refers to RC(=O)N, wherein R is alkyl, alkylidenyl, aryl, heteroaryl and the like.

The term "imino" refers to —C=N—[H or C—].
The term "nitro" refers to —NO$_2$.
The term "trifluoromethyl" refers to —CF$_3$.
The term "trifluoromethoxy" refers to —OCF$_3$.
The term "cyano" refers to —CN.
The term "hydroxy" or "hydroxyl" refers to —OH.
The term "oxy" refers to —O—.
The term "thio" refers to —S—.
The term "thioxo" refers to (=S).
The term "keto" refers to (=O).

As used herein, the term "salt" refers to a complex formed between a charged molecule and a suitable counterion to form a neutral species. Example of salts for positively charged compounds include but are not limited to fluoride, chloride, bromide, iodide, acetate, sulfate, nitrate, citrate, oxalate, bicarbonate and the like. Examples of salts for negatively charged compounds include, but are not limited to sodium, potassium, cesium, calcium, magnesium, ammonium, dimethylammonium, triethylammonium and the like.

The term "pharmaceutically acceptable salt" refers to a formulation of a compound that does not abrogate the biological activity and properties of the compound. Pharmaceutical salts can be obtained by reacting a compound of the invention with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like. Pharmaceutical salts can also be obtained by reacting a compound of the invention with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, and salts with amino acids such as arginine, lysine, and the like.

The term "protecting group" refers to a chemical functionality designed to temporarily block a portion of a molecule from chemical modification during synthetic steps. An extensive list of such protecting groups can be found in "*Protective Groups in Organic Synthesis*", 4th Edition, 2006, by Theodora W. Greene & Peter G. M. Wuts.

The terms "opiate" or "opioid" and refers to any agent, natural or synthetic, capable of specifically binding to an opioid receptor, including opium or any of its derivatives (e.g., morphine), as well as synthetic or semi-synthetic derivatives.

"Treating," "treatment," or "therapy" of a disease or disorder means slowing, stopping, or reversing progression of the disease or disorder, as evidenced by a reduction or elimination of either clinical or diagnostic symptoms, using the compositions and methods of the present invention as described herein. These terms do not necessarily mean total cure. Any alleviation of any undesired signs or symptoms of the disease to any extent or the slowing down of the progress of the disease can be considered treatment. Furthermore, treatment may include acts that may worsen the patient's overall feeling of well being or appearance. Treatment may also include lengthening the life of the patient, even if the symptoms are not alleviated, the disease conditions are not ameliorated, or the patient's overall feeling of well being is not improved.

"Preventing," "prophylaxis," or "prevention" of a disease or disorder means prevention of the occurrence or onset of a disease or disorder or some or all of its symptoms.

"Addiction" as used herein refers to a disease or disorder characterized by a habitual psychological and physiologic dependence on a substance or practice that is substantially beyond voluntary control. Addictions amenable to treatment using the compounds and methods described herein include substance addictions such as, e.g., addictions to narcotics (e.g., morphine, heroin), alcohol, and nicotine, as well as behavioral addictions such as, e.g., addiction to gambling.

The term "therapeutically effective regime" means that a pharmaceutical composition or combination thereof is administered in sufficient amount and frequency and by an appropriate route to ameliorate the disease or disorder, or to at least detectably prevent, delay, inhibit, or reverse development of at least one symptom or biochemical marker of a disease or disorder amenable to treatment by modulation of an analgesic receptor.

The term "therapeutically effective amount" refers to an amount of an agent of the present invention, or a combination of an agent of the present invention with other agent(s), that is present to achieve a desired result, e.g., reducing addition to a substance of abuse, or preventing, delaying, inhibiting, or reversing a symptom or biochemical marker of a disease or disorder amenable to treatment by modulation of an analgesic receptor, when administered in an appropriate regime.

The phrase "administering a compound to a subject" refers to preparing a formulation of a compound and administering the compound to the subject by whatever means, e.g., orally, parenterally, intravenously, etc. The phrase "contacting a subject with a compound" refers to contacting any cell or organ of the subject with the compound. Thus, if a subject ingests the prodrug of a compound and, in the subject's body, the prodrug is converted into the compound, by these definitions, the prodrug is administered to the subject and the subject is contacted with the compound.

As to any of the above groups, which contain one or more substituents, it is understood that such groups do not contain any substitution or substitution patterns which are sterically impractical and/or synthetically non-feasible. In addition, the compounds of this invention include all stereochemical isomers arising from the substitution of these compounds.

Obviously, numerous modifications and variations of the present invention are possible in light of the above teachings. It is therefore to be understood that within the scope of the appended claims, the invention may be practiced otherwise than as specifically described herein.

Compounds

In one embodiment, disclosed are compounds of the following Formula I:

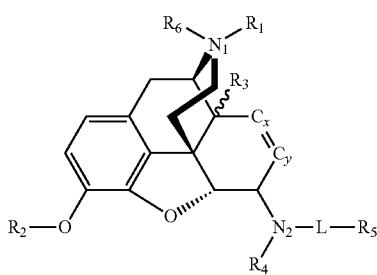

(I)

or a pharmaceutically acceptable salt thereof,
where
$R_1$ is selected from the group consisting of hydrogen, optionally substituted alkyl, optionally substituted alkenyl, optionally substituted alkynyl, optionally substituted cycloalkyl, optionally substituted cycloalkenyl, optionally substituted aryl, and optionally substituted heteroaryl;
$R_2$ is selected from the group consisting of hydrogen, optionally substituted alkyl, optionally substituted alkenyl, optionally substituted optionally substituted alkynyl, and optionally substituted alkanoyl;
$R_3$ is selected from the group consisting of hydrogen, OH, and optionally substituted alkoxy;
$R_4$ is selected from the group consisting of hydrogen, optionally substituted alkyl, optionally substituted alkenyl, optionally substituted alkynyl, optionally substituted cycloalkyl, optionally substituted cycloalkenyl, optionally substituted aryl, and optionally substituted heteroaryl;
L is a group linking $N_2$ and $R_5$ consisting of a bond, $CH_2$, C=O, S(=O)$_2$, (C=O)—NH—, and (C=O)—O—;
$R_5$ is selected from the group consisting of hydrogen, optionally substituted alkyl, optionally substituted alkenyl, optionally substituted alkynyl, optionally substituted cycloalkyl, optionally substituted cycloalkenyl, optionally substituted aryl, and optionally substituted heteroaryl;
$R_6$ is selected from the group consisting of hydrogen, O$^-$, $CH_3$, and optionally substituted alkoxy, or $R_6$ is absent;
$N_1$ is a nitrogen atom, which is neutral when $R_6$ is absent, or is charged when $R_6$ is present, to satisfy the normal valence of a tertiary or quaternary nitrogen;
$N_2$ is a nitrogen atom, which is bound to the opiate nucleus in α or β stereochemistry or a mixture thereof; and
$C_x$ and $C_y$ together form an alkylidene group (—$CH_2$—$CH_2$—) or alkenylidene group (—CH=CH—); any of the attached hydrogens may be replaced to form a substituted alkenylidene group or substituted alkylidene of any possible stereochemistry.

In some embodiments, the alkyl group in $R_1$, $R_2$, $R_4$, and $R_5$, or the alkyl group in the alkanoyl group of $R_2$, or the alkyl group in the alkoxy group of $R_3$, is an optionally substituted $C_1$-$C_{20}$ alkyl. In other embodiments, the alkyl is an optionally substituted $C_1$-$C_{10}$ alkyl. In some embodiments, the alkyl is an optionally substituted $C_1$-$C_5$ alkyl. In some of these embodiments, the alkyl is selected from the group consisting of methyl, ethyl, isopropyl, 2-methyl-1-propyl, cyclopropymethyl, cyclobutylmethyl, allyl, 2-methyl-2-propenyl, 2-buten-1-yl, 3-methyl-2-buten-1-yl, 2,3-dimethyl-2-buten-1-yl, benzyl, Hydroxy-1'-methylalkyl, cyclohexenyl methyl; dihydrofuranyl methyl, and tetrahydrofuranylmethyl.

In some embodiments, the alkenyl group in $R_1$, $R_2$, $R_4$, and $R_5$ is an optionally substituted $C_2$-$C_{20}$ alkenyl. In other embodiments, the alkenyl is an optionally substituted $C_2$-$C_{10}$ alkenyl. In some embodiments, the alkenyl is an optionally substituted $C_2$-$C_5$ alkenyl.

In some embodiments, the alkynyl group in $R_1$, $R_2$, $R_4$, and $R_5$ is an optionally substituted $C_2$-$C_{20}$ alkynyl. In other embodiments, the alkynyl is an optionally substituted $C_2$-$C_{10}$ alkynyl. In some embodiments, the alkynyl is an optionally substituted $C_2$-$C_5$ alkynyl.

In some embodiments, the cycloalkyl group in $R_1$, $R_2$, $R_4$, and $R_5$ is an optionally substituted $C_3$-$C_{20}$ cycloalkyl. In other embodiments, the cycloalkyl is an optionally substituted $C_3$-$C_{10}$ cycloalkyl. In some embodiments, the cycloalkyl is an optionally substituted $C_3$-$C_6$ cycloalkyl.

In some embodiments, the aryl group in $R_1$, $R_4$, and $R_5$ is a 6-membered optionally substituted aryl. In some embodiments, the aryl group is a bicyclic or tricyclic ring structure. An aryl is a moiety in which at least one of the rings in the multicyclic structure is an aryl group. The other rings may or may not be aromatic. In some embodiments, the aryl group is an optionally substituted phenyl, optionally substituted naphthyl, optionally substituted 1,2,3,4-tetrahydronaphthalene, or optionally substituted 2,3-dihydro-1H-indene.

In some embodiments, the heteroaryl group in $R_1$, $R_4$, and $R_5$ is a 5 or 6-membered optionally substituted heteroaryl. In some embodiments, the heteroaryl group has 1-3 nitrogen atoms in the ring. In other embodiments, the heteroaryl group has 1-3 oxygen atoms in the ring. In some embodiments, the heteroaryl group has 1-3 sulfur atoms in the ring. In further embodiments, the heteroaryl has a combination of 1-3 nitrogen, oxygen, or sulfur atoms. In some embodiments, the heteroaryl group is a bicyclic or tricyclic ring structure. A heteroaryl is a moiety in which at least one of the rings in the multicyclic structure is a heteroaryl group. The other rings may or may not be aromatic and may or may not contain a heteroatom in the ring backbone.

In some embodiments, $R_3$ is connected such that the stereochemistry at its attachment point is R. In other embodiments, the stereochemistry at the point of attachment of $R_3$ is S.

In another embodiment, the compound of Formula (I) has an opiate nucleus that is selected from the group consisting of a nalmefene, naloxone, naltrexone, a morphan, and a morphinan. Thus,
  a nalmefene or naltrexone core is one in which $R_1$ is cyclopropylmethyl, $R_2$ is hydrogen, $R_3$ is hydroxy, $R_6$ is absent, and $C_x$—$C_y$ is $CH_2$—$CH_2$;
  a naloxone core is one in which $R_1$ is $CH_2$=CH—$CH_2$—, $R_2$ is hydrogen, $R_3$ is hydroxy, $R_6$ is absent, and $C_x$—$C_y$ is $CH_2$—$CH_2$;
  a morphine is one in which $R_1$ is methyl, $R_2$ is hydrogen, $R_3$ is hydrogen, $R_6$ is absent, and $C_x$—$C_y$ is CH=CH; and
  a morphinan core is one in which $R_1$ is hydrogen, $R_3$ is hydrogen, $R_6$ is absent, and $C_x$—$C_y$ is $CH_2$—$CH_2$.

In some embodiments, disclosed herein is a compound of Formula I, where
$R_1$ is selected from the group consisting of hydrogen, $C_1$-$C_5$ optionally substituted alkyl, $C_2$-$C_5$ optionally substituted alkenyl, $C_2$-$C_5$ optionally substituted alkynyl, $C_3$-$C_6$ optionally substituted cycloalkyl, $C_3$-$C_6$ optionally substituted cycloalkenyl, $C_6$-$C_{12}$ optionally substituted aryl, and 5 or 6-membered optionally substituted heteroaryl containing 1-3 nitrogen, oxygen, or sulfur atoms, or a combination thereof
$R_2$ is selected from the group consisting of hydrogen, $C_1$-$C_5$ optionally substituted alkyl, $C_2$-$C_5$ optionally substituted alkenyl, $C_2$-$C_5$ optionally substituted alkynyl, $C_3$-$C_6$ optionally substituted cycloalkyl, $C_3$-$C_6$ optionally substituted cycloalkenyl, $C_6$-$C_{12}$ optionally substituted aryl, 5 or 6-membered optionally substituted heteroaryl containing 1-3 nitrogen, oxygen, or sulfur atoms, or a combination thereof and $C_2$-$C_6$ optionally substituted alkanoyl;

$R_3$ is selected from the group consisting of hydrogen, OH, and $C_1$-$C_6$ Alkoxy;

$R_4$ is selected from the group consisting of hydrogen, $C_1$-$C_5$ optionally substituted alkyl, $C_2$-$C_5$ optionally substituted alkenyl, $C_2$-$C_5$ optionally substituted alkynyl, $C_3$-$C_6$ optionally substituted cycloalkyl, $C_3$-$C_6$ optionally substituted cycloalkenyl, $C_6$-$C_{12}$ optionally substituted aryl, 5 or 6-membered optionally substituted heteroaryl containing 1-3 nitrogen, oxygen, or sulfur atoms, or a combination thereof; and $R_5$ is $C_6$-$C_{12}$ optionally substituted aryl, or 5 or 6-membered optionally substituted heteroaryl containing 1-3 nitrogen, oxygen, or sulfur atoms, or a combination thereof.

In other embodiments, disclosed herein is a compound of Formula I, where $R_1$ is selected from the group consisting of hydrogen, methyl, ethyl, isopropyl, 2-methyl-1-propyl, cyclopropymethyl, cyclobutylmethyl, allyl, 2-methyl-2-propenyl, 2-buten-1-yl, 3-methyl-2-buten-1-yl, 2,3-dimethyl-2-buten-1-yl, benzyl, Hydroxy-1'-methylalkyl, cyclohexenyl methyl; dihydrofuranyl methyl, and tetrahydrofuranylmethyl;

$R_2$ is selected from the group consisting of hydrogen, methyl, and acetyl $R_3$ is hydrogen or OH;

$R_4$ is hydrogen or methyl;

L is C=O; and $R_6$ is selected from the group consisting of hydrogen, O⁻, and $CH_3$, or $R_6$ is absent.

In another aspect, disclosed herein are the following compounds and pharmaceutically acceptable salts thereof:

naltrexone oxime;
6-α-naltrexamine;
6-β-naltrexamine;
6-α-N-methylnaltrexamine;
6-β-N-methylnaltrexamine;
6-β-(4'-methyl)benzamido-14-hydroxy-17-(cyclopropylmethyl)nordesmorphine;
6-β-(4'-methyl)benzamido-14-hydroxy-17-(cyclopropylmethyl)nordesmorphine oxalate;
6-β-(4'-trifluoromethyl)benzamido-14-hydroxy-17-(cyclopropylmethyl)nordesmorphine;
6-β-(4'-trimethylfluoro)benzamido-14-hydroxy-17-(cyclopropylmethyl)nordesmorphine-oxalate;
6-β-(4'-bromo)benzamido-14-hydroxy-17-(cyclopropylmethyl)nordesmorphine;
6-β-(4'-bromo)benzamido-14-hydroxy-17-(cyclopropylmethyl)nordesmorphine-oxalate;
6-β-(4'-iodo)benzamido-14-hydroxy-17-(cyclopropylmethyl)nordesmorphine;
6-β-(4'-bromo)benzamido-14-hydroxy-17-(cyclopropylmethyl)nordesmorphine-oxalate;
6-β-(4'-iodo)benzamido-14-hydroxy-17-(cyclopropylmethyl)nordesmorphine;
6-β-(4'-iodo)benzamido-14-hydroxy-17-(cyclopropylmethyl)nordesmorphine-oxalate;
6-(4'-t-butyl)benzamido-14-hydroxy-17-(cyclopropylmethyl)nordesmorphine;
6-β-(4'-t-butyl)benzamido-14-hydroxy-17-(cyclopropylmethyl)nordesmorphine-oxalate;
6-β-(3',4'-dichloro)benzamido-14-hydroxy-17-(cyclopropylmethyl)nordesmorphine;
6-β-(3',4'-dichloro)benzamido-14-hydroxy-17-(cyclopropylmethyl)nordesmorphine hydrochloride;
6-β-(4'-chloro)benzamido-14-hydroxy-17-(cyclopropylmethyl)nordesmorphine;
6-β-(4'-chloro)benzamido-14-hydroxy-17-(cyclopropylmethyl)nordesmorphine hydrochloride;
6-β-(3'-cyano)benzamido-14-hydroxy-17-(cyclopropylmethyl)nordesmorphine;
6-(3'-N-hydroxycarbamimidoyl)benzamido-14-hydroxy-17-(cyclopropylmethyl)nordesmorphine;
6-α-(4'-trifluoromethyl)-N-methylbenzamido-14-hydroxy-17-(cyclopropylmethyl)nordesmorphine;
6-α-(4'-trifluoromethyl)-N-methylbenzamido-14-hydroxy-17-(cyclopropylmethyl)nordesmorphine oxalate;
6-α-(4'-trifluoromethyl)-N-methylbenzamido-14-hydroxy-17-(cyclopropylmethyl)nordesmorphine oxalate;
6-β-(4'-trifluoromethyl)-N-methylbenzamido-14-hydroxy-17-(cyclopropylmethyl)nordesmorphine;
6-β-(4'-trifluoromethyl)-N-methylbenzamido-14-hydroxy-17-(cyclopropylmethyl)nordesmorphine oxalate;
6-α-(4'-bromo)-N-methylbenzamido-14-hydroxy-17-(cyclopropylmethyl)nordesmorphine;
6-α-(4'-bromo)-N-methylbenzamido-14-hydroxy-17-(cyclopropylmethyl)nordesmorphine oxalate;
6-β-(4'-bromo)-N-methylbenzamido-14-hydroxy-17-(cyclopropylmethyl)nordesmorphine;
6-β-(4'-bromo)-N-methylbenzamido-14-hydroxy-17-(cyclopropylmethyl)nordesmorphine oxalate;
6-α-(4'-iodo)-N-methylbenzamido-14-hydroxy-17-(cyclopropylmethyl)nordesmorphine;
6-α-(4'-iodo)-N-methylbenzamido-14-hydroxy-17-(cyclopropylmethyl)nordesmorphine oxalate;
6-β-(4'-iodo)-N-methylbenzamido-14-hydroxy-17-(cyclopropylmethyl)nordesmorphine;
6-β-(4'-iodo)-N-methylbenzamido-14-hydroxy-17-(cyclopropylmethyl)nordesmorphine oxalate;
6-α-(4'-t-butyl)-N-methylbenzamido-14-hydroxy-17-(cyclopropylmethyl)nordesmorphine;
6-α-(4'-t-butyl)-N-methylbenzamido-14-hydroxy-17-(cyclopropylmethyl)nordesmorphine oxalate;
6-β-(4'-t-butyl)-N-methylbenzamido-14-hydroxy-17-(cyclopropylmethyl)nordesmorphine;
6-β-(4'-t-butyl)-N-methylbenzamido-14-hydroxy-17-(cyclopropylmethyl)nordesmorphine oxalate;
6-α-(4'-chloro)-N-methylbenzamido-14-hydroxy-17-(cyclopropylmethyl)nordesmorphine;
6-α-(4'-chloro)-N-methylbenzamido-14-hydroxy-17-(cyclopropylmethyl)nordesmorphine oxalate;
6-β-(4'-chloro)-N-methylbenzamido-14-hydroxy-17-(cyclopropylmethyl)nordesmorphine;
6-β-(4'-chloro)-N-methylbenzamido-14-hydroxy-17-(cyclopropylmethyl)nordesmorphine oxalate;
6-α-(3',4'-dichloro)-N-methylbenzamido-14-hydroxy-17-(cyclopropylmethyl)nordesmorphine;
6-α-(3',4'-dichloro)-N-methylbenzamido-14-hydroxy-17-(cyclopropylmethyl)nordesmorphine oxalate;
6-β-(3',4'-dichloro)-N-methylbenzamido-14-hydroxy-17-(cyclopropylmethyl)nordesmorphine;
6-β-(3',4'-dichloro)-N-methylbenzamido-14-hydroxy-17-(cyclopropylmethyl)nordesmorphine oxalate;
17-cyclopropylmethyl-3,14-β-dihydroxy-4,5-α-epoxy-6-α-trans-3-(3-furyl)acrylamido]morphinan;
17-cyclopropylmethyl-3,14-β-dihydroxy-4,5-α-epoxy-6-α-trans-3-(3-furyl)acrylamido]morphinan oxalate;
17-cyclopropylmethyl-3,14-β-dihydroxy-4,5-α-epoxy-6-β-[-trans-3-(3-furyl)acrylamido]morphinan;
17-cyclopropylmethyl-3,14-β-dihydroxy-4,5-α-epoxy-6-β-[-trans-3-(3-furyl)acrylamido]morphinan oxalate;
17-cyclopropylmethyl-3,14-β-dihydroxy-4,5-α-epoxy-6-α-[N-methyl-trans-3-(3-furyl)acrylamido]morphinan;

17-cyclopropylmethyl-3,14-β-dihydroxy-4,5-α-epoxy-6-α-[N-methyl-trans-3-(3-furyl)acrylamido]morphinan oxalate;
17-cyclopropylmethyl-3,14-β-dihydroxy-4,5-α-epoxy-6-β-[N-methyl-trans-3-(3-furyl)acrylamido]morphinan;
17-cyclopropylmethyl-3,14-β-dihydroxy-4,5-α-epoxy-6-β-[N-methyl-trans-3-(3-furyl)acrylamido]morphinan oxalate;
6-β-(4'-bromo)benzamido-14-hydroxy-17-N,N-(cyclopropylmethyl)oxynordesmorphine;
17-Cyclopropylmethyl-3,14-β-dihydroxy-4,5-α-epoxy-6-β-[(4'-methyl)benzamido]morphinan-N-oxide;
17-Cyclopropylmethyl-3,14-β-dihydroxy-4,5-α-epoxy-6-β-[(4'-trifluoromethyl)benzamido]morphinan-N-oxide;
17-Cyclopropylmethyl-3,14-β-dihydroxy-4,5-α-epoxy-6-β-[(4'-tert-butyl)benzamido]morphinan-N-oxide;
17-Cyclopropylmethyl-3,14-β-dihydroxy-4,5-α-epoxy-6-β-[(4'-dimethylamino)benzamido]morphinan-N-oxide;
17-Cyclopropylmethyl-3,14-β-dihydroxy-4,5-α-epoxy-6-β-[(thiophen-2'-yl)acetamido]morphinan-N-oxide;
17-Cyclopropylmethyl-3,14-β-dihydroxy-4,5-α-epoxy-6-α-N-methyl[(4'-bromo)benzamido]morphinan-N-oxide;
17-Cyclopropylmethyl-3,14-β-dihydroxy-4,5-α-epoxy-6-β-N-methyl[(4'-tert-butyl)benzamido]morphinan-N-oxide;
17-Cyclopropylmethyl-3,14-β-dihydroxy-4,5-α-epoxy-6β-N-methyl[(3',4'-dichloro)benzamido]morphinan-N-oxide;
17-Cyclopropylmethyl-3,14-β-dihydroxy-4,5-α-epoxy-6-β-[(3',4'-dimethoxy)benzamido]morphinan-N-oxide;
17-Cyclopropylmethyl-3,14-β-dihydroxy-4,5-α-epoxy-6-β-[(3'-methoxy)benzamido]morphinan-N-oxide;
17-Cyclopropylmethyl-3,14-β-dihydroxy-4,5-α-epoxy-6-β-(benzamido)morphinan-N-oxide;
17-Cyclopropylmethyl-3,14-β-dihydroxy-4,5-α-epoxy-6β-(phenylacetamido)morphinan-N-oxide;
17-Cyclopropylmethyl-3,14-β-dihydroxy-4,5-α-epoxy-6-β-[(3'-hydroxy)benzamido]morphinan-N-oxide;
17-Cyclopropylmethyl-3,14-β-dihydroxy-4,5-α-epoxy-6-β-[(4'-chloro)benzamido]morphinan-N-oxide;
17-Cyclopropylmethyl-3,14-β-dihydroxy-4,5-α-epoxy-6-α-(6-acetamido-2,3,4,6-tetra-O-benzyl-D-pyranose)morphinan-N-oxide;
17-Cyclopropylmethyl-3,14-β-dihydroxy-4,5-α-epoxy-6-α-(benzamido)morphinan-N-oxide;
17-Cyclopropylmethyl-3,14-β-dihydroxy-4,5-α-epoxy-6-β-[(4'-carbomethoxy)benzamido]morphinan-N-oxide;
17-Cyclopropylmethyl-3,14-β-dihydroxy-4,5-α-epoxy-6-β-[(4'-methoxy)phenylacetamido]morphinan N-oxide;
17-Cyclopropylmethyl-3,14-β-dihydroxy-4,5-α-epoxy-6-α-[(3',4'-dimethoxy)benzamido]morphinan-N-oxide;
17-Cyclopropylmethyl-3,14-β-dihydroxy-4,5-α-epoxy-6-β-[(3'-methoxy)benzamido]morphinan-N-oxide;
17-Cyclopropylmethyl-3,14-β-dihydroxy-4,5-α-epoxy-6-β-[(3',4'-dichloro)benzamido]morphinan-N-oxide;
17-Cyclopropylmethyl-3,14-β-dihydroxy-4,5-α-epoxy-6-β-[N-methyl-trans-3-(3-furyl)acrylamido]morphinan-N-oxide;
17-Cyclopropylmethyl-3,14-β-dihydroxy-4,5-α-epoxy-6-α-N-methyl-[(4'-trifluoromethyl)benzamido]morphinan-N-oxide;
17-Cyclopropylmethyl-3,14-β-dihydroxy-4,5-α-epoxy-6-α-N-methyl-[(4'-bromo)benzamido]morphinan-N-oxide;
17-Cyclopropylmethyl-3,14-β-dihydroxy-4,5-α-epoxy-6-α-N-methyl-[(4'-iodo)benzamido]morphinan-N-oxide;
17-Cyclopropylmethyl-3,14-β-dihydroxy-4,5-α-epoxy-6-α-N-methyl-[(4'-tert-butyl)benzamido]benzamido]morphinan-N-oxide;
17-Cyclopropylmethyl-3,14-β-dihydroxy-4,5-α-epoxy-6-β-[(4'-carboxy)benzamido]morphinan-N-oxide;
17-Cyclopropylmethyl-3,14-β-dihydroxy-4,5-α-epoxy-6-α-N-methyl-[(4'-chloro)benzamido]morphinan-N-oxide;
17-Cyclopropylmethyl-3,14-β-dihydroxy-4,5-α-epoxy-6-α-N-methyl-(3',4'-dichloro)morphinan-N-oxide;
17-Cyclopropylmethyl-3,14-β-dihydroxy-4,5-α-epoxy-6-β-[(3'-(N''-hydroxycarbamimidoyl)benzamido]morphinan-N-oxide;
17-Cyclopropylmethyl-3,14-β-dihydroxy-4,5-α-epoxy-6-β-[(3' cyano)benzamido]-morphinan-N-oxide;
17-Cyclopropylmethyl-3,14-β-dihydroxy-4,5-α-epoxy-6β-N-methyl-[(4'-iodo)benzamido]morphinan-N-oxide;
17-Methyl-3,14-β-dihydroxy-4,5-α-epoxy-6-β-[(4'-methyl)benzamido]-morphinan-N-oxide;
17-Cyclopropylmethyl-3,14-β-dihydroxy-4,5-α-epoxy-6-β-[(3'-fluoro-4'-trifluoromethyl)benzamido]morphinan-N-oxide;
17-Cyclopropylmethyl-3,14-β-dihydroxy-4,5-α-epoxy-6-β-[(4'-methylsulfonyl)benzamido]morphinan-N-oxide;
17-Cyclopropylmethyl-3,14-β-dihydroxy-4,5-α-epoxy-6-β-[(4'-chloro-3'-fluoro)benzamido]morphinan-N-oxide;
17-Cyclopropylmethyl-3,14-β-dihydroxy-4,5-α-epoxy-6β-N-methyl-(4'-bromo) morphinan-N-oxide;
17-Cyclopropylmethyl-3,14-β-dihydroxy-4,5-α-epoxy-6β-N-methyl-(4'-trifluoromethyl)morphinan-N-oxide;
17-Cyclopropylmethyl-3,14-β-dihydroxy-4,5-α-epoxy-6β-N-methyl-(4'-iodo)morphinan-N-oxide;
17-Cyclopropylmethyl-3,14-β-dihydroxy-4,5-α-epoxy-6-β-[(4'-bromo)benzamido]morphinan-N-oxide;
17-Cyclopropylmethyl-3,14-β-dihydroxy-4,5-α-epoxy-6-β-N-methyl-(4'-chloro)morphinan-N-oxide;
17-Cyclopropylmethyl-3,14-β-dihydroxy-4,5-α-epoxy-6-β-[(3'-methoxy)benzamido]morphinan-N-oxide;
17-Cyclopropylmethyl-3,14-β-dihydroxy-4,5-α-epoxy-6-β-[(4'-iodo)benzamido]-morphinan-N-oxide;
17-Cyclopropylmethyl-3,14-β-dihydroxy-4,5-α-epoxy-6-β-[(2-oxo-2H-chromene)-6-sulfonamido]morphinan;
17-Cyclopropylmethyl-3,14-β-dihydroxy-4,5-α-epoxy-6-β-[(2-oxo-2H-chromene)-6-sulfonamido]morphinan hydrochloride;
17-Cyclopropylmethyl-3,14-β-dihydroxy-4,5-α-epoxy-6-β-[(5'-dimethylamino)naphthalene sulfonamido]morphinan; and
17-Cyclopropylmethyl-3,14-β-dihydroxy-4,5-α-epoxy-6-β-[(5'-dimethylamino)naphthalene sulfonamido]morphinan hydrochloride.

The compounds provided herein can be synthesized using well-known synthetic organic chemistry techniques. Standard synthetic pathways that are used in synthesizing some of the compounds disclosed herein. Those skilled in the art will recognize that these examples are meant to illustrate and not limit the present disclosure.

Additional synthetic procedures are described in the Examples section below.

Methods of Use

The methods of use described herein reflect the discovery that the compounds provide superior and unexpected efficacy in reducing the self-administration of alcohol and other substances of abuse (e.g., cocaine). Opioid receptors are well-characterized receptors and numerous studies suggest that alcohol and cocaine interact with endogenous opioid systems. Antagonizing opioid receptors decrease the effects of pleasure-inducing endogenous opioids. By attenuating the positive reinforcing effects of alcohol and cocaine consumption, opioid receptor antagonists have direct effects on alcohol-seeking behavior. A decrease in alcohol consumption by antagonism of opioid receptors suggests direct effects on this reinforcement system and animal studies have shown that μ-, δ- and κ-opioid receptors contribute to alcohol-induced reinforcement.

Herein, we report the design of a class of metabolically stable compounds that have mixed potency and efficacy as μ-, δ- and κ-opioid receptor partial agonists, inverse-agonists and/or antagonists as alcohol and drug self-administration cessation (addiction cessation) agents. Partial agonist agents show a dual action by inhibiting reinforcement and stimulating dopamine release to decrease craving. The rationale for the work described herein was to develop long-lived, metabolically stable analogues of naltrexone or nalmefene by replacing the metabolically labile 6-keto or 6-methylene groups, respectively, with an amide moiety, thus leading to agents with sustained pharmacological activity and potentially less hepatotoxicity.

Thus, in some embodiments, the compounds of Formula I disclosed herein are antagonists of μ-, δ-, or κ-opioid receptors. In other embodiments, the compounds of Formula I disclosed herein are partial antagonists of μ-, δ-, or κ-opioid receptors. In yet other embodiments, the compounds of Formula I disclosed herein are partial agonists of μ-, δ-, or κ-opioid receptors. In further embodiments, the compounds of Formula I disclosed herein are inverse agonists of μ-, δ-, or κ-opioid receptors. In certain embodiments, the compounds of Formula I disclosed herein are partial inverse agonists of μ-, δ-, or κ-opioid receptors.

The chemical synthesis of a series of substituted aryl amide derivatives of 6-β-naltrexamine 4-10 was efficiently accomplished and used to characterize the structural requirements for binding to and functional activity of human μ-, δ-, κ-opioid and nociceptin receptors. Compound 1a was converted to its oxime 2 in quantitative yield using hydroxylamine hydrochloride in the presence of sodium acetate in refluxing ethanol. Reduction of the oxime 2 to the corresponding amine 3 was accomplished by heating 2 with borane-tetrahydrofuran complex for 2 days. Following an aqueous workup, amine 3 was obtained as a 1:9 (α/β) mixture of diastereomers. The diastereomers were separated by chromatography on silica gel and the stereochemistry at the C-6 position was determined on the basis of the size of the NMR coupling constant, $J_{5,6}$. The amine 3 (only the beta diastereomer was used in this work because previous work showed little stereoselectivity in opioid binding for β versus α diastereomers) was coupled either with a carboxylic acid in the presence of benzotriazol-1-yl-oxy-tris-(dimethylamino) phosphonium hexa-fluorophosphate (BOP) and diisopropylethylamine or alternatively, with an acid chloride in triethylamine. The product was treated with potassium carbonate in methanol to remove the byproduct resulting from esterification of the 3-position hydroxyl group, giving amides 4-10 in moderate to high yields (60-97%). While the BOP coupling procedure resulted in less esterification at the 3-position compared with the acid chloride method, some esterification at the 3-position could not be avoided. Thus, it was found to be more convenient to run the reaction with an excess of the acid derivative to aid in the purification of the intermediate amide ester.

The binding of compounds 1a, 1b, 4-10 to the μ-, δ- and κ-opioid receptors was determined in a competitive binding assay (see Example 68) with the following radioligands: [³H][D-ala², N-MePhe⁴, Gly-ol]enkephalin, 11 ([³H]DAMGO, μ-opioid receptor agonist), [³H][D-ala², D-leu⁵]enkephalin, 12 ([³H]DADLE, δ-opioid receptor agonist) and [³H](5a,7a,8b)-(+)-N-methyl-N-(7-[1-pyrrolidinyl]-1-oxaspiro[4,5]dec-8-yl)-benzeneacetamide, 13 ([³H]U69593, κ-opioid receptor agonist). Results of binding to the individual receptors, and the ratios of δ- and κ-binding relative to the μ-receptor were summarized and listed in Tables 1a and 1b. Amides 4-10 were between 4 and 10-fold more potent at the δ-opioid receptors than 1a and 1b ($K_i$<4 nM for 4-10 compared to 16.3 and 13.3 nM for 1a and 1b, respectively). The 3,4-dichloro phenyl amide and the bulky t-butyl and iodo phenyl amide analogs were the most potent with $K_i$ values around 1 nM. Compared to 1a and 1b, binding was also improved with regard to the κ-opioid receptor. The phenylamide derivative afforded a $K_i$<0.4 nM compared to 1a ($K_i$=0.81 nM) and 1b ($K_i$=1.03 nM). The p-methyl phenyl analog 4 bound the κ receptor with the greatest affinity ($K_i$=0.11 nM) suggesting that a smaller group at the para position was favored for κ receptor binding. Finally, adding an aryl amide at the 6-position on the naltrexamine core (i.e., 4-10) did not significantly change the affinity for binding to the μ-receptor compared to 1a and 1b, (i.e., $K_i$ values between 0.3 to 1.09 nM were observed). With respect to binding, compounds 4 and 6 were greater than three-fold more selective for the κ- than for the μ- or δ-receptors. All the compounds examined had at least 2-3 fold greater potency for the κ-receptor compared to the μ- or δ-receptor. Compound 5 was about 7-fold more selective for the κ-receptor compared with the δ-receptor.

TABLE 1a

Inhibition Values and Selectivity for μ, δ and κ opioid binding:

| | $K_i$ (nM) ± SEM | | | Selectivity | |
|---|---|---|---|---|---|
| Compd[a] | μ | δ | κ | δ/μ | κ/μ |
| 1a | 0.30 ± 0 | 16.31 ± 1.10 | 0.81 ± 0.02 | 49 | 2.5 |
| 1b | 0.91 ± 0.10 | 13.26 ± 0.75 | 1.03 ± 0.19 | 15 | 1.1 |
| 4 | 0.34 ± 0.05 | 3.6 ± 0.3 | 0.11 ± 0.02 | 11 | 0.32 |
| 5 | 0.47 ± 0.05 | 2.5 ± 0.3 | 0.34 ± 0.05 | 5.3 | 0.72 |
| 6 | 0.88 ± 0.10 | 2.2 ± 0.3 | 0.29 ± 0.04 | 2.5 | 0.33 |
| 7 | 0.82 ± 0.10 | 1.4 ± 0.2 | 0.37 ± 0.05 | 1.7 | 0.45 |
| 8 | 1.09 ± 0.20 | 1.4 ± 0.1 | 0.37 ± 0.06 | 1.3 | 0.34 |
| 9 | 0.48 ± 0.07 | 1.0 ± 0.1 | 0.34 ± 0.04 | 2.1 | 0.71 |
| 10 | 0.61 ± 0.09 | 2.6 ± 0.3 | 0.23 ± 0.03 | 4.3 | 0.38 |
| 11 | 0.9 | | | | |
| 17 | | 0.8 | | | |
| Salvonorin A | | | 0.8 | | |

Compounds 4-10 were oxalic salts. Ki values were expressed as the mean ± SEM of two determinations.

TABLE 1b

Inhibition of Agonist binding at opioid receptors by Compounds 21-63
$K_i$ (nM) ± SEM

| Compound ID | μ | δ | κ |
|---|---|---|---|
| 21 | 5.5 ± 0.2 | 342.0 ± 12.59 | 3.1 ± 0.16 |
| 22 | 1.4 ± 0.03 | 117.0 ± 5.18 | 1.9 ± 0.11 |
| 23 | 1.7 ± 0.07 | 25.0 ± 2.38 | 1.9 ± 0.14 |
| 24 | 477.8 ± 23 | 5849.0 ± 559.67 | 227.0 ± 48.12 |
| 25 | 34.8 ± 2.08 | 752.0 ± 8.91 | 13.0 ± 1.0 |
| 26 | 5.8 ± 0.21 | 51.0 ± 5.8 | 2.41 ± 0.19 |

TABLE 1b-continued

Inhibition of Agonist binding at opioid receptors by Compounds 21-63
$K_i$ (nM) ± SEM

| Compound ID | μ | δ | κ |
|---|---|---|---|
| 27 | 714.0 ± 66 | 535.0 ± 43.78 | 72.0 ± 12.64 |
| 28 | 196.0 ± 11 | <50% inh | 367.0 ± 33 |
| 29 | 37.0 ± 2 | 621.0 ± 16.2 | 71.0 ± 4.87 |
| 30 | 16.0 ± 1 | 444.0 ± 39.07 | 9.7 ± 0.95 |
| 31 | 114.0 ± 6 | <50% inh | 100.0 ± 11 |
| 32 | 28.0 ± 2 | 813.0 ± 33.98 | 8.5 ± 0.92 |
| 33 | 43 ± 3 | 1404.0 ± 40.52 | 47.0 ± 4 |
| 34 | 34 ± 2 | 1166.0 ± 100.52 | 49.0 ± 4 |
| 35 | 4.7 ± 0.12 | 219.0 ± 7.97 | 1.8 ± 0.1 |
| 36 | 307.6 ± 13 | 1860 ± 143.83 | 18.0 ± 1 |
| 37 | 37.0 ± 2.6 | 822 ± 124 | 64.0 ± 10 |
| 38 | 30.0 ± 2.1 | 1389 ± 279 | 51.0 ± 6 |
| 39 | 78.0 ± 20 | 472.0 ± 78 | 10.0 ± 1 |
| 40 | 38.0 ± 6.5 | 590.0 ± 590? | 6.7 ± 0.4 |
| 41 | 16.0 ± 2.7 | 51.0 ± 2.45 | 30.0 ± 3 |
| 42 | 49.0 ± 8.6 | 1054.0 ± 38 | 16.0 ± 2 |
| 43 | 3.6 ± 0.43 | 212.0 ± 11 | 2.0 ± 0.2 |
| 44 | 65.0 ± 7.7 | 2507.0 ± 231 | 3.9 ± 0.5 |
| 45 | 13.4 ± 0.6 | 148.3 ± 12 | 4.9 ± 0.4 |
| 47 | 27.6 ± 0.8 | 290.0 ± 17 | 5.9 ± 0.4 |
| 48 | 26.0 ± 2 | 148.0 ± 10 | 14.0 ± 1 |
| 50 | 368.9 ± 18 | 3331.0 ± 160 | 77.0 ± 8 |
| 51 | 7.3 ± 0.2 | 120.0 ± 5 | 2.0 ± 0.09 |
| 52 | 114.2 ± 3.3 | 1223.0 ± 45 | 26.0 ± 1.81 |
| 53 | 116.7 ± 7.8 | <50% inh | 426.0 ± 21.55 |
| 54 | 147.6 ± 9.3 | 3058 ± 271 | 117.0 ± 10.03 |
| 55 | 244.3 ± 8.2 | <50% inh | 1185.0 ± 133.6 |
| 56 | 8.3 ± 0.3 | 352.0 ± 10 | 3.8 ± 0.3 |
| 58 | 23.8 ± 0.9 | 187.0 ± 9 | 9.2 ± 075 |
| 59 | 14.1 ± 0.5 | 390.0 ± 18 | 2.5 ± 0.09 |
| 60 | 193.4 ± 7.4 | 5086.0 ± 384 | 168.0 ± 7.97 |
| 61 | 378.4 ± 18.8 | 1642.0 ± 94 | 195.0 ± 17.18 |
| 62 | 408.1 ± 11.5 | <50% inh | 224.0 ± 15.65 |
| 63 | 7.0 ± 0.1 | 246.0 ± 15 | 6.3 ± 0.6 |

A functional assay was also run in order to evaluate the opioid receptor-mediated activation of its associated G protein. Compounds 4-10 were evaluated using the [$^{35}$S]GTPγS assay. In this assay, a compound's potency or affinity for the receptor was associated with its $EC_{50}$ value for stimulating [$^{35}$S]GTPγS binding. Agonist activity of each compound was determined at the μ-, δ-, κ-opioid and NOP-receptors, and compared to the standard selective full agonists, 11, [D-pen2, D-pen5]-enkephalin, 14 (DPDPE), 13 and nociceptin, 15, respectively. Table 2 summarizes the $EC_{50}$ and $E_{max}$ values for compounds 4 to 16 in the presence of cloned human cell membranes containing the μ, δ- or κ-opioid or NOP receptors.

Para-alkyl substituted 4 and 8 were either very weak agonists or completely not functional suggesting that electron donating groups might be detrimental to functional activity. The 3,4-dichlorophenyl derivative 9 was found to stimulate GTPγS binding as a full agonist at μ-, δ- and κ-opioid receptors ($E_{max}$ ~80-85%), with an $EC_{50}$ value in the low nanomolar range ($EC_{50}$=2.3, 1.4, 0.9 for μ-, δ-, κ-receptors, respectively). Compounds 5-7 and 10 were partial agonists ($E_{max}$ values between 28-63%) at μ-, δ-, and κ-opioid receptors (Table 2). Compounds 4-10 had very low affinity for the NOP receptor and did not stimulate agonist-induced GTPγS binding.

TABLE 2

Stimulation of [$^{35}$S]GTPγS binding at opioid receptors by compounds 4-10 and the opioid agonists, 11, 14, 15 and 16

| Compd[a] | μ | | δ | | κ | | NOP | |
|---|---|---|---|---|---|---|---|---|
| | $EC_{50}$ (nM) | $E_{max}$ (%) | $EC_{50}$ (nM) | $E_{max}$ (%) | $EC_{50}$ (nM) | $E_{max}$ (%) | $EC_{50}$ (nM) | $E_{max}$ (%) |
| 4 | >10 μM | 0 | 0.14 ± 0.1 | 10 ± 9.6 | >10 μM | 0 | >10 μM | 0 |
| 5 | 16 ± 2.1 | 63 ± 14 | 5.1 ± 0.2 | 28 ± 6.5 | 9.9 ± 1.7 | 36 ± 6.4 | >10 μM | 0 |
| 6 | 4.5 ± 0.5 | 38 ± 4.3 | 0.2 ± 0.1 | 46 ± 3.7 | 0.1 ± 0.1 | 42 ± 3.9 | >10 μM | 0 |
| 7 | 8.8 ± 1.7 | 53 ± 2.8 | 5.1 ± 2.9 | 45 ± 6.2 | 29 ± 3.4 | 28 ± 3.1 | >10 μM | 0 |
| 8 | >10 μM | 0 | >10 μM | 0 | >10 μM | 0 | >10 μM | 0 |
| 9 | 2.3 ± 1.4 | 85 ± 7.4 | 1.4 ± 1.4 | 85 ± 35 | 0.9 ± 0.1 | 80 ± 7.4 | >10 μM | 0 |
| 10 | 6.8 ± 1.7 | 46 ± 3.8 | 42 ± 3.1 | 22 ± 1.7 | 7.1 ± 2.7 | 31 ± 2.6 | >10 μM | 0 |
| 11 | 8.2 ± 1.4 | 124 ± 7.9 | — | — | — | — | — | 0 |
| 14 | — | — | 15 ± 2.6 | 76 ± 4.8 | — | — | — | 0 |
| 15 | — | — | — | — | — | — | 3.9 ± 0.5 | 109 ± 11 |
| 16 | — | — | — | — | 0.4 ± 0.2 | 54 ± 14 | — | 0 |

Compounds 4-10 were oxalic salts. $E_{max}$ values are expressed as mean ± SEM percentage of basal [$^{35}$S]GTPγS binding stimulation.

In a second functional assay, compounds 4-10 were evaluated as inverse-agonists. Compounds 4 and 8 were found to be partial inverse-agonists at the μ- and κ-receptors. Compounds 4-10 were found to potently decrease basal binding and compounds 7 and 9 were found to have high affinity as inverse-agonists at the NOP (Nociceptin) receptor. Compound 8 was also observed to be a potent inverse-agonist at δ- and κ-receptors, with less potent inverse-agonism at the μ-receptor (Table 3). Compound 4 was found to be a potent inverse-agonist at μ- and κ-receptors with decreased potency (albeit with high efficacy) at the NOP receptor. Compound 6 was also observed to display inverse-agonism at the δ-receptor albeit at higher concentrations (i.e., 10 nM-10 μM), in addition to potent agonism at lower concentrations (i.e., 10 pM-10 nM).

TABLE 3

Inhibition of basal [$^{35}$S]GTPγS binding at opioid receptors by compounds 4-10.

| | μ | | δ | | κ | | NOP | |
|---|---|---|---|---|---|---|---|---|
| Compd | $EC_{50}$ (nM) | $E_{max}$ (%) | $EC_{50}$ (nM) | $E_{max}$ (%) | $EC_{50}$ (nM) | $E_{max}$ (%) | $EC_{50}$ (nM) | $E_{max}$ (%) |
| 4 | 8.9 ± 0.2 | 3 ± 2.4 | >10 μM | | 2.4 ± 0.4 | 20 ± 1.2 | 135 ± 31 | 138 ± 4.8 |
| 5 | >10 μM | 0 | >10 μM | 0 | >10 μM | 0 | 20 ± 11 | 104 ± 4.4 |
| 6 | >10 μM | 0 | 66 ± 1.8 | 35 ± 4.8 | >10 μM | 0 | 94 ± 33 | 92 ± 7.4 |
| 7 | >10 μM | 0 | >10 μM | 0 | >10 μM | 0 | 3.6 ± 1.5 | 173 ± 6.3 |
| 8 | 4.0 ± 0.1 μM | 46 ± 1.6 | 0.3 ± 0.1 | 28 ± 9.1 | 0.4 ± 1.2 | 60 ± 2.6 | 15 ± 2.6 | 92 ± 2.9 |
| 9 | >10 μM | 0 | >10 μM | 0 | >10 μM | 0 | 0.1 ± 0.4 | 87 ± 6.9 |
| 10 | >10 μM | 0 | >10 μM | 0 | >10 μM | 0 | 88 ± 19 | 320 ± 6.8 |

Compounds 4-10 were oxalic salts. $E_{max}$ values are expressed as mean ± SEM percentage of basal [$^{35}$S]GTPγS binding stimulation.

High affinity compounds that showed low or partial agonist activity in the GTPγS binding experiment were tested for inhibition of agonist-induced GTPγS binding at each receptor. Compound 4 produced strong inhibition at δ- and κ-receptors and potent inhibition at μ-receptors, but not at the NOP-receptor (Table 4). Compound 5 produced potent inhibition at both κ- and NOP-receptors, but not at μ- or δ-receptors. Compound 6 produced very potent inhibition at the κ-receptor but no detectable inhibition at μ-, δ- or NOP receptors. Compounds 7 and 8 did not produce any detectable inhibition at any opioid receptor examined. Compounds 4, 5 and 6 appear to possess mixed activity as either agonists, inverse-agonists or antagonists for each of the μ-, δ- and κ-opioid and NOP-receptors. As described below, further kinetic analysis was done to characterize the pharmacological properties of these latter compounds.

TABLE 4

Inhibition of agonist-stimulated [$^{35}$S]GTPγS binding at opioid receptors by compounds 4-8[a] compared to 1a, 17 and 18.

| | $K_i$ | | | |
|---|---|---|---|---|
| Compd | μ | δ | κ | NOP |
| 4 | 6.2 ± 1.9 nM | 0.1 ± 0.02 nM | 15 ± 1.4 pM | >10 μM |
| 5 | >10 μM | >10 μM | 637 ± 10 pM | 4.2 ± 0.3 nM |
| 6 | >10 μM | >10 μM | 0.3 ± 0.2 pM | >10 μM |
| 7 | >10 μM | >10 μM | >10 μM | >10 μM |
| 8 | >10 μM | >10 μM | >10 μM | >10 μM |
| 1a | 3.6 ± 0.2 nM | 66.8 ± 12.6 nM | 42 ± 4.0 pM | >10 μM |
| 17 | — | 0.3 ± 0.1 nM | — | — |
| 18 | — | — | 4.8 ± 2.3 pM | — |

[a]Compounds 4-8 were oxalic salts. Values are expressed as mean (±SEM) $K_i$ for inhibition of 11 (1 μM), 14 (200 nM), 16 (2 μM) and 15 (NOP; 1 μM) basal [$^{35}$S]GTPγS binding stimulation was performed with μ-, δ-, κ-opioid and nociceptin (NOP) receptors, respectively.

The SAR of the aromatic amide portion of the opioid derivatives was examined. Despite the limited number of compounds studied, a few conclusions could be reached. In general, electron withdrawing para-monosubstituted or meta, para-disubstituted aromatic groups showed the greatest potency and efficacy for the μ-receptor (Table 2). Thus, compound 10 (the 4-chloro-substituted aromatic amide) showed significant affinity for the μ-receptor and had $EC_{50}$ values in the low nM range (Tables 1 and 2). Electron-rich aryl-substituted compounds 4 and 8 showed no detectable stimulation of [$^{35}$S]GTPγS binding. Compounds 4 and 6 possessed the greatest potency against the δ receptor but aside from compound 9, the compounds tested did not markedly stimulate [$^{35}$S]GTPγS binding. With the exception of the electron rich aryl-substituted compounds 4 and 8, all of the compounds examined had relatively good potency for the κ-receptor. The efficacy of 4-10 for the κ receptor largely paralleled that observed for the μ receptor. No detectable potency for the NOP receptor was observed for compounds 4-10 (Table 2). In summary, the opioid receptors appear to favor binding of compounds with highly electron-deficient and lipophilic substituents at the meta and para position of C-6 substituted aromatic amides of naltrexamine. The electronic effect of the aromatic substituent on the in vivo $ED_{50}$ value was more pronounced (see in vivo analysis, below).

As a prelude to studying the test compounds in vivo, TLC- and HPLC-based analytical methods and biochemical assays were used to assess the metabolic stability of selected compounds in the presence of rat, mouse and human liver preparations and the appropriate NADPH generating system. These studies were done to ascertain the stability of the compounds toward oxidative metabolism in advance of more detailed studies with highly purified human CYPs and FMO3 as well as to determine if the compounds possessed sufficient metabolic stability for in vivo studies. Compared to 1b, the candidate compounds 4-9 were quite metabolically stable in the presence of liver preparations from all three species examined (i.e., rat, mouse, human) (Table 5).

TABLE 5

Metabolic Stability of 4-9 in the presence of liver preparations

| | Half Life (mins) | | |
|---|---|---|---|
| Compound | Rat | Mouse | Human |
| 1b | 100 | 20 | 20 |
| 4 | 373 | NC[c] | NC[c] |
| 5 | 379 | NC[c] | NC[c] |
| 6 | 97 | 273 | NC[c] |
| 7 | 164 | 480 | 112 |
| 8 | 94 | NC[c] | 555 |
| 9 | 135 | NC[c] | 301 |

Compounds 4-9 were oxalic salts. NC, No Change

Compounds 4 and 5 remained unchanged in the mouse and human liver microsomes for the length of the experiment. Compounds 6 to 9 were also very stable in the mouse and human liver microsomes with a half life greater than 112 minutes. Similarly, 4 to 9 were stable in mouse liver microsomes and compounds that were metabolically stable in the presence of mouse or human liver microsomal preparations did not afford evidence of significant amounts of metabolite formation based on inspection of the HPLC profiles (data not shown). In the presence of rat liver microsomes, overall, the compounds were somewhat less metabolically stable, but the half life values observed did not preclude evaluation of the compounds in vivo. The lack of metabolic instability, however, may have been the result of inhibition of CYP-dependent metabolism. To examine this point more carefully, the effect of 4-9 on inhibition of selected CYPs was examined.

CYP Inhibition: it is known that cyclopropyl methyl-containing amines can inhibit CYP. To understand the metabolic stability data described above and to examine the possible extent and selectivity of CYP inhibition, selected compounds (i.e., 4-9) were examined along with 1b for their ability to inhibit selective functional activities of human CYP enzymes. The observed percent inhibition for selective functional inhibition of CYP-3A4, -2B6, -2C9, -2C19 and -2D6 were reported in Table 6.

TABLE 6

Percent Inhibition of CYP3A4, CYP2B6, CYP2C9, CYP2C19 and CYP2D6 by Selected Naltrexamides.

| Compd[a] | Percent Inhibition[b] | | | | |
|---|---|---|---|---|---|
| | CYP3A4 | CYP2B6 | CYP2C9 | CYP2C19 | CYP2D6 |
| 1b | 60 | 5 | 35 | 17 | 31 |
| 4 | 36 | 6 | 12 | 7 | ND[c] |
| 5 | 29 | 9 | 9 | 52 | 12 |
| 6 | 36 | 18 | 8 | 19 | 12 |
| 7 | 41 | 6 | 7 | 17 | ND |
| 8 | 13 | 9 | 5 | 49 | ND |
| 9 | 11 | 5 | 7 | 39 | 10 |

[a]Compounds 4-9 were oxalic salts.
[b]Percent inhibition in the presence of 10 μM test compound. The test compound was preincubated for 2-5 min with the enzyme and cofactor and then the appropriate substrate was added and the rate of product was monitored and compared with the complete system without the test compound present.
Values are the average of 2-3 determinations.
The range of the values never exceeded 10-15%.
ND, no detectable inhibition was observed at the concentration of the test compound examined.

The enzyme assays were done using standard conditions as previously described. Compounds 4-9 were weaker inhibitors than 1b for the CYPs studied except in the case of CYP2C19 that appeared to be more sensitive than 1b to inhibition by 5, 8, and 9. In general, the enzymes mainly involved in inhibition by 4-9 were CYP3A4 and 2C19. In addition, compound 6 inhibited CYP2B6 with greater potency than 1b. Replacement of the C-6 exo methylene group of 1b with an aryl amide group in this series attenuated the inhibitory potency toward CYP. This suggests a significant contribution of the C-6 moiety in the interaction of 1b with CYP and for the C-6 substituted amides examined herein, it suggests a decreased interaction with CYP. Because CYP3A4 and CYP2D6 often make significant contributions to opioid metabolism, adverse drug-drug interactions, metabolic bioactivation and therefore possible side-effects, this new synthetic class of opioid analog is attractive. Decreased interaction with CYP in part may explain some of the metabolic stability observed for the compounds in this and related series. On the basis of the data from the in vitro metabolism studies, we judged the compounds to be sufficiently stable and of low CYP inhibitory potency to study them in vivo in an animal model of ethanol self-administration. Compound 6 was selected to examine the putative metabolism in greater detail.

A radiometric assay and an HPLC assay were set up to examine the possible metabolism of radiolabelled 6. Compound 6 was chosen as a representative compound to study because its radiosynthesis was very efficient. To confirm the results from the radiometric studies, we developed an HPLC method to analyze N-oxygenation and amide hydrolysis of compound 6. In the presence of rat liver microsomes and after extractive work-up and HPLC analysis, compound 6 hydrolysis was linearly dependent on time (0-15 min) and protein concentration (i.e., 0-0.4 mg of protein). However, the rate of hydrolysis was quite low and ranged between 0.7 to 0.9 nmol/min/mg of protein. No significant amount of the N-oxide of 6 was detected. In the presence of human liver microsomes, compound 6 hydrolysis was linearly dependent on time (0-30 min) and protein concentration (i.e., 0-0.5 mg of protein). The rate of hydrolysis in human liver microsomes was lower than for rat liver microsomes and ranged between 0.2 to 0.5 nmol/min/mg of protein. In contrast to rat liver microsomes, in the presence of human liver microsomes a significant amount of 6 N-oxide was formed (i.e., 10-23 pmol/min/mg of protein). Formation of the N-oxide of 6 was dependent on pH; the rate doubled upon going from pH 7.4 to pH 10. Highly purified human FMO3 catalyzed the formation of 6 N-oxide (i.e., 0.9 to 1.1 nmol/min/mg of protein) but this rate was quite low. In summary, overall, the metabolism of 6 was quite low and the data agreed with the relative metabolic stability described above (Table 5).

The oxalate salt of radiolabelled 6 was administered to two groups of three male Wistar rats via oral gavage (400 μg/kg) and i.v. (100 μg/kg) route of administration. After oral administration, the $T_{max}$ was 57 min and the apparent $T_{1/2}$ was 2.5 h. After i.v. administration, the $T_{max}$ was 22 min and the $T_{1/2}$ was 45 mins. A separate group of three male Wistar rats was administered the oxalate salt of radiolabelled 6 via the oral route of administration and sacrificed after 1.5 h. Brain tissue and blood was immediately procured and chilled on ice and prepared for analysis as described in the Methods section. The amount of radiolabelled 6 oxalate present in each animal at 1.5 h was determined by examining an aliquot of brain homogenate and plasma by scintillation counting. The amount of radiolabelled 6 in brain tissue and plasma was 6.5±0.8 ng/gm and 2.8±0.3 ng/mL, respectively. The brain tissue:plasma ratio of 2.3 at the time of measurement suggested that adequate brain concentrations of 6 was present to proceed with in vivo alcohol self-administration cessation studies.

In Vivo Alcohol Self-Administration Studies:

In vivo studies were intended to test the effects of compounds 4-10 on baseline ethanol (EtOH) intake in rats trained to self-administer a 10% (w/v) ethanol solution, utilizing an operant technique model. This model is commonly used to examine the effects of novel compounds on reinforcing effects of ethanol. Control groups consisting of rats trained to orally self-administer a 0.025% saccharin (SACC) solution were used to examine non-specific effects of the experimental compounds. 1b hydrochloride was used as a positive control. Initially, dose range studies were conducted and if compounds appeared biologically active, more detailed studies were conducted. Preliminary determinations, showed that 4-8 and 10 possessed $ED_{50}$ values of 0.25, 0.019, 0.042, 0.038, 0.05 and 0.5 mg/kg, respectively. Because compound 10 showed inhibition of alcohol self-administration with an $ED_{50}$ of approximately 0.5 mg/kg and was considerably less potent than the other compounds examined, it was not studied further. Additionally, after s.c. administration of 0.025 mg/kg of 9, a potent decrease in alcohol consumption was observed (i.e., 77%), but 9 also caused profound analgesia and consequently further studies were not pursued with this compound. Compounds 5-8 were then administered s.c. in a separate drug-naive cohort of rats using a within-subjects Latin Square dose design. Results from testing compounds 5-8 at doses ranging from 0.00625 to 0.05 mg/kg showed significant effects in the self-administration model (Table 7).

TABLE 7

Effect of 5-8[a] on the number of ethanol self-administrations in rats.

| Compd | N | Vehicle | Dose (μg/kg) 6.25 | 12.5 | 25 | 50 |
|---|---|---|---|---|---|---|
| 1b | 10 | 39.6 ± 3.2 | ND[c] | 26.1 ± 3.8[b] | 22.2 ± 3.4[b] | 17.1. ± 1.5[b] |
| 5 | 10 | 30.6 ± 3.9 | 26.4 ± 3.6 | 20.5 ± 3.2[b] | 12.8 ± 1.6[b] | ND[c] |
| 6 | 10 | 41.1 ± 6.0 | ND[c] | 29.7 ± 3.9[b] | 25.6 ± 3.5[b] | 19.3 ± 2.6[b] |
| 7 | 10 | 33.3 ± 5.5 | ND[c] | 25.0 ± 2.7 | 24.7 ± 3.7 | 13.3 ± 1.5[b] |
| 8 | 10 | 39.2 ± 5.4 | ND[c] | 35.6 ± 5.7 | 28.0 ± 3.1 | 19.9 ± 4.1[b] |

[a]Compounds 5-8 were oxalic salts.
[b]Statistically significant compared to vehicle-treated rats (P <0.05).
[c]ND, no data collected at this dose based on preliminary screening in a separate cohort of rats showing no efficacy at this dose (for 6.25 μg/kg dose) or total suppression of saccharin controls (for 50 μg/kg dose).

For 1b [F=13.1, P<0.0001], 5 [F=5.3, P<0.006], and 6 [F=7.3, P<0.001], treatment with opioid 30 min prior to testing had an overall effect on operant self-administration of 10% ethanol. Compared with vehicle, post hoc analysis of 1b, 5 and 6 showed that doses of 0.0125, 0.025 and 0.05 mg/kg significantly inhibited operant self-administration of 10% ethanol. For compounds 7 [F=5.7, P<0.004] and 8 [F=4.9, P<0.008], treatment had an overall effect on operant self-administration of 10% ethanol. Compared with vehicle, post hoc analysis showed that only a dose of 0.05 mg/kg significantly inhibited operant self-administration of 10% ethanol. To test whether the effect of the compounds were selective for ethanol, the effect of 1b and 5-8 on self-administration of saccharin (0.025%) (Table 8) was examined.

TABLE 8

Effect of 5-8[a] on the number of saccharin self-administrations in one hour in rats.

| Compd | N | Vehicle | Dose (μg/kg) 6.25 | 12.5 | 25 | 50 |
|---|---|---|---|---|---|---|
| 1b | | 21.0 ± 10.6 | ND[c] | 17.5 ± 6.0 | 7.3 ± 1.9 | 13.7 ± 5.6 |
| 5 | 6 | 33.3 ± 7.2 | 23.8 ± 6.8 | 24.8 ± 8.0 | 10.0 ± 3.1[b] | ND[c] |
| 6 | 6 | 31.5 ± 9.1 | ND[c] | 11.3 ± 3.6 | 13.2 ± 2.3 | 10.5 ± 5.2[b] |
| 7 | 6 | 16.8 ± 7.0 | ND[c] | 6.0 ± 1.7 | 6.2 ± 3.0 | 4.8 ± 1.6 |
| 8 | 6 | 14.0 ± 7.1 | ND[c] | 16.2 ± 8.8 | 6.2 ± 2.3 | 7.2 ± 3.5 |

[a]Compounds 5-8 were oxalic salts.
[b]Statistically significant compared to vehicle-treated rats (P < 0.05).
[c]ND, no data collected at this dose based on preliminary screening in separate cohort of rats showing no efficacy at this dose (for 6.25 μg/kg dose) or total suppression of saccharin controls (for 50 μg/kg dose).

Treatment with 1b [F=1.0, P=0.4135] and 8 [F=0.68.7, P=0.578] did not have an overall effect on the operant self-administration of saccharin compared with vehicle. Compound 5 [F=6.06, P=0.0065], compound 6 [F=4.52, P=0.019], and compound 7 [F=3.7, P=0.037] did have an overall effect on saccharin self-administration. In light of these non-specific effects, post-hoc analysis of a dose of 0.025 mg/kg for 5 and a dose of 0.05 mg/kg for 6 showed that these doses were the only doses examined that significantly inhibited self-administration of saccharin, compared with vehicle. The $ED_{50}$ value for ethanol self-administration observed for hydrochlorides of 1a and 1b in similar experiments was approximately 0.5 and 0.04 mg/kg, respectively. The efficacy for inhibition of ethanol self-administration by 5-8 compared very favorably to that of 1b, and in some cases, (i.e., compounds 5, 6 and 7) were apparently more efficacious.

In vivo SAR. The effect of the C-6 meta- or para-aryl amide substituent of the opioid on the relative efficacy of compounds 5-9 to inhibit ethanol self-administration in vivo was examined with regression correlation analysis using various physical organic parameters. A plot of the log $ED_{50}$ value versus the electronic substituent sigma values provided a linear correlation with a slope of rho ($\rho$) value of 1.55 and an $R^2$ value of 0.925. A plot of the log $ED_{50}$ value versus the hydrophobicity substituent pi values provided a less linear correlation with a slope of 1.35 and an $R^2$ value of 0.59. Likewise, an examination of steric effects with a plot of the log $ED_{50}$ value versus the steric substituent values (Fs) provided a non-linear correlation with a slope of −0.793 and an $R^2$ value of 0.563. On the basis of the $R^2$ value and the goodness of fit the suggestion is that the in vivo $ED_{50}$ values for alcohol cessation can be explained to a great extent by the C-6 meta- or para-aryl amide electronic substituent effects and to a much less extent on the basis of hydrophobicity or steric effects.

Cocaine Self Administration:

We tested the hypothesis that increased cocaine self-administration with extended access was associated with increased activity of the kappa opioid system in rats. Rats self-administered 0.5 mg/kg/injection of cocaine on a fixed-ratio (FR) schedule in either one-hour (short access, ShA) or six-hour (long access, LgA) sessions. After cocaine intake in the LgA rats increased to a maximum, the effects of three kappa (κ) opioid receptor antagonists were tested on cocaine intake in ShA and LgA rats. Cocaine self-administration increased under FR and progressive-ratio (PR) schedules in LgA rats. Nor-BNI, a κ receptor antagonist, decreased cocaine intake in LgA rats under a PR schedule whereas naltrexone and 6-oxalate, a nonselective opioid receptor antagonist and a partial agonist, respectively decreased cocaine intake in both groups. The present study showed that inhibition of κ opioid receptors attenuated only the increased cocaine intake in LgA rats under a PR schedule whereas inhibition of μ and κ receptors decreased cocaine intake in both ShA and LgA groups. The data suggest that increased motivation for cocaine in rats with extended access may be related to increased K opioid activity and may contribute to compulsive use.

Data, as shown in FIG. 1, are expressed as the number of injections on the left axis and mg/kg on the right axis. Error bars are SEM values. Open symbols are the data in rats with one-hour access to cocaine (ShA). Filled symbols are the data in rats with six-hour access (LgA). The left panel shows the data from an entire session for each group, and the right panel shows the data from the first hour of a 6-hr session in LgA rats and from a 1-hr session in ShA rats. *p<0.05, ***p<0.001 compared with session 1.

Effect of extended access to cocaine self-administration: Under all conditions, LgA rats produced a significant increase in cocaine self-administration whereas ShA rats maintained a constant level of intake during the period of extended access for the LgA rats. For example, in the group of rats that were tested with 6-oxalate and 15 mg/kg of nor-BNI, cocaine self-administration in LgA rats significantly increased within a session as well as during the first hour of a session [FIG. 1; First hour intake: Session×Access interaction, $F_{14,196}$=2.26, p<0.01, Session, $F_{14,196}$=5.88, p<0.001, Access, $F_{1,196}$=4.79, p<0.05; Session intake: Session×Access interaction, $F_{14,196}$=6.84, p<0.001, Session, $F_{14,196}$=8.85, p<0.001, Access, $F_{1,196}$=195.0, p<0.001]. No significant change in cocaine self-administration was observed in ShA rats. After extended access to cocaine self-administration, LgA rats achieved a higher breakpoint for 0.5 mg/kg/injection of cocaine self-administration than ShA rats under a PR schedule in all groups [Student t-test, the 6-oxalate/nor-BNI (15 mg/kg) group, p<0.05; the nor-BNI (30 mg/kg) group, p<0.01; the naltrexone group, p<0.01].

Figure 2:
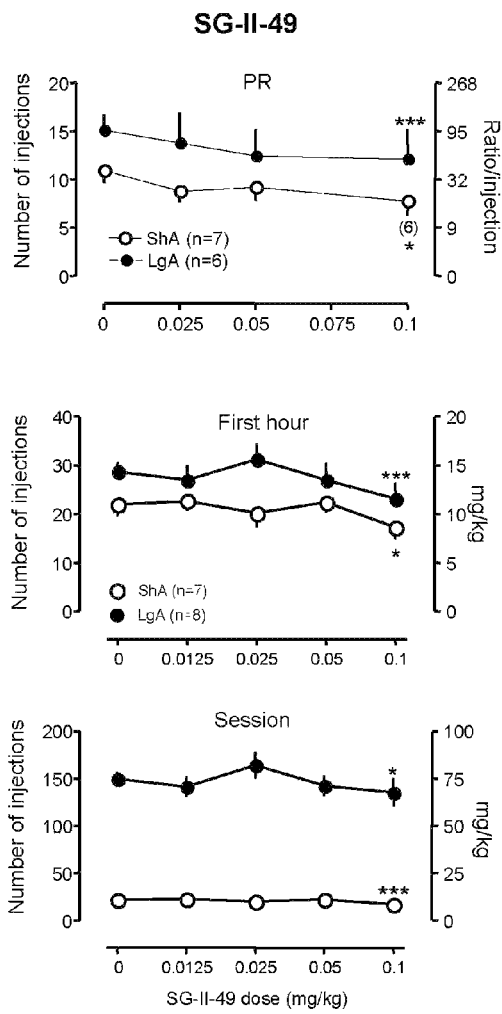
FIG. 2 shows graphs depicting the effect of 6-Oxalate (SG-II-49) on cocaine self-administration.

Effect of 6-Oxalate, a Non-Selective Opioid Receptor Partial Agonist, on Cocaine Self-Administration:

Pretreatment with 6-oxalate significantly decreased cocaine intake in both ShA and LgA rats under an FR schedule [FIG. 2; First hour intake: Dose×Access interaction, $F_{4,52}=2.49$, $p<0.05$, Dose, $F_{4,52}=7.5$, $p<0.001$, Access, $F_{1,52}=3.0$, $p>0.05$; Session intake: Dose×Access interaction, $F_{4,52}=3.69$, $p<0.05$, Dose, $F_{4,52}=7.47$, $p<0.001$, Access, $F_{1,52}=177.0$, $p<0.001$]. Similarly, 6-oxalate dose-dependently decreased cocaine self-administration under a PR schedule in both ShA and LgA groups (Dose, $F_{3,33}=6.98$, $p<0.001$) with no significant interaction between Dose and Access.

Pharmacodynamic Profiles of 6-Oxalate at Opioid Receptors:

In the opioid receptor binding assay, 6-oxalate showed high affinity for $\mu$, $\delta$ and $\kappa$ receptors with approximately a 3-fold difference in affinity among receptors. In the GTPγS functional binding assay, 6-oxalate stimulated all three receptors with 38 to 46%.

Data, as shown in FIG. 2, are expressed as the number of injections on the left axis and ratio/injection (top) or mg/kg (middle, bottom) on the right axis. Error bars are SEM values. The abscissa represents the dose of 6-Oxalate (SG-II-49). Doses of 6-Oxalate (SG-II-49) were subcutaneously injected into rats 30 minutes before each test session. *p<0.05, ***p<0.001 compared with vehicle.

Summary:

6-Oxalate was developed as a pharmacotherapeutic candidate for alcoholism based on opioid receptor binding and functional data. The data show that 6-oxalate was a non-selective partial agonist at three opioid receptors. Several studies have previously focused on the identification of therapeutic agents with partial agonistic property at $\mu$ receptors to avoid withdrawal symptoms after the cessation of the treatment. Buprenorphine, a potent $\mu$ receptor partial agonist with $\kappa$ receptor antagonistic activity, inhibits cocaine self-administration in monkeys. Similar results were reported in rats. Buprenorphine also decreases the rewarding effect of cocaine in rats when measured in conditioned place preference. Thus, our hypothesis was that a partial blockade of both $\mu$ and $\kappa$ opioid receptors would decrease cocaine self-administration both in ShA and LgA rats. Indeed, 6-oxalate decreased cocaine self-administration in both groups. More importantly, 6-oxalate dose-dependently decreased cocaine self-administration under a PR schedule to a similar extent in ShA and LgA rats suggesting that the drug decreased the motivation to self-administer cocaine in both groups.

In conclusion, the present study shows that the inhibition of $\kappa$ opioid receptors selectively attenuated increased cocaine self-administration under a PR schedule in rats with extended access whereas the inhibition of $\mu$ opioid receptors decreased cocaine self-administration in ShA and LgA rats. Therefore, the data suggest that increased motivation to self-administer cocaine in rats with extended access may be associated with enhanced activity of the $\kappa$ opioid system and antagonism of the $\kappa$ opioid system may afford cocaine (and other drugs of abuse) cessation agents.

Addiction Cessation Agents.

The addiction cessation agents disclosed herein are useful in a variety of applications relating to modulation of opioid receptor signaling within the nervous system. The agents are also useful for the treatment of diseases or disorders amenable to amelioration via modulation of opioid receptor signaling (e.g., diseases or disorders of the CNS). Such diseases or disorders include various addictions. Addictions amenable to treatment using the agents described herein include, for example, addictions to drugs such as narcotics (e.g., morphine, heroin, and other opiates), nicotine, alcohol and cocaine, as well as behavioral addictions (e.g., gambling addiction).

Accordingly, disclosed herein are pharmaceutical compositions and methods for the treatment of addictions and other CNS-related disorders. The addiction cessation agents of the present invention can be delivered or administered to a mammal, (e.g., human subject), alone, in the form of a pharmaceutically acceptable salt or hydrolysable precursor thereof, or in the form of a pharmaceutical composition wherein the compound is mixed with suitable carriers or excipient(s) in a therapeutically effective amount. In a preferred embodiment, for treating a drug addiction in a subject and when administered in an appropriate therapeutically effective regime, a sufficient amount of the addiction cessation agent is present to inhibit opioid receptors in vivo so as to predispose the subject to ingest lower amounts of a drug or undergo an addictive behavior.

The addiction cessation agents or metabolites that are used in the methods disclosed herein can be administered as pharmaceutical compositions comprising the agent together with one or more other pharmaceutically acceptable component. Pharmaceutical compositions can be in the form of solids (i.e., powders, granules, dragees, tablets, or pills), semi-solids (i.e., gels, slurries, or ointments), liquids, or gases (i.e., aerosols or inhalants).

Suitable formulations for use in the present invention are found in, for example, [*Remington's Pharmaceutical Sciences*, Mack Publishing Company, Philadelphia, Pa., 17th ed. (1985) and Langer, *Science*, 249:1527-1533 (1990)]. The pharmaceutical compositions described herein can be manufactured in a conventional manner, e.g., mixing, dissolving, granulating, dragee-making, levigating, emulsifying, encapsulating, entrapping, or lyophilizing processes.

A pharmaceutically acceptable salt is a non-toxic metal, alkaline earth metal, or an ammonium salt commonly used in the pharmaceutical industry including, for example, a sodium, potassium, lithium, calcium, magnesium, barium, ammonium, and protamine zinc salt, which is prepared by methods well-known in the art. The term also includes a non-toxic acid addition salt, which is generally prepared by treating the compounds of the present invention with a suitable organic or inorganic acid. Representative salts include, e.g., hydrochloride, hydrobromide, sulfate, bisulfate, acetate, oxalate, valerate, oleate, laurate, borate, benzoate, lactate, phosphate, tosylate, citrate, maleate, fumarate, succinate, tartrate, and napsylate.

The addiction cessation agents can be formulated with common excipients, diluents or carriers, and compressed into tablets, or formulated as elixirs or solutions for convenient oral administration. The agents can also be formulated as sustained release dosage forms and the like.

Pharmaceutical compositions suitable for use in accordance with the present invention include compositions wherein the active ingredients are contained in a therapeutically effective amount. The therapeutically effective amounts for the methods of the present invention can depend on a variety of factors, including, e.g., age, body weight, general health, sex, diet, time and manner of administration, rate of excretion, drug combination, the judgment of the treating physician, and the severity of the particular affliction being treated. The amount of active agent will also depend upon the specific activity of the opiate-related agent and whether that agent is co-administered with any other therapeutic or prophylactic ingredients.

The invention will be further described by the following examples, meant to illustrate but not limit the invention.

EXAMPLES

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention. The following examples are offered to illustrate, but not to limit the claimed invention.

The following general information applies with respect to the synthesis and analysis of compounds set forth in the Examples. The synthesis of the target molecules is outlined in Scheme 1. While not limiting, some representative examples are provided in Scheme 1. $^1$H NMR and $^{13}$C NMR were recorded at 300.0 and 75.4 MHz, respectively, on a Varian Mercury 300 instrument. Chemical shifts were reported in ppm (δ) relative to CDCl$_3$ at 7.26 ppm and 77 ppm, respectively. NMR spectra were recorded in CDCl$_3$ unless stated otherwise. Melting points were reported uncorrected. High resolution mass spectra were obtained with a VG 7070 spectrometer with an Opus V3.1 and DEC 3000 Alpha Station data system or a Waters LCT Premier instrument operating in the ESI mode.

Scheme 1: Synthesis of Naltrexamides

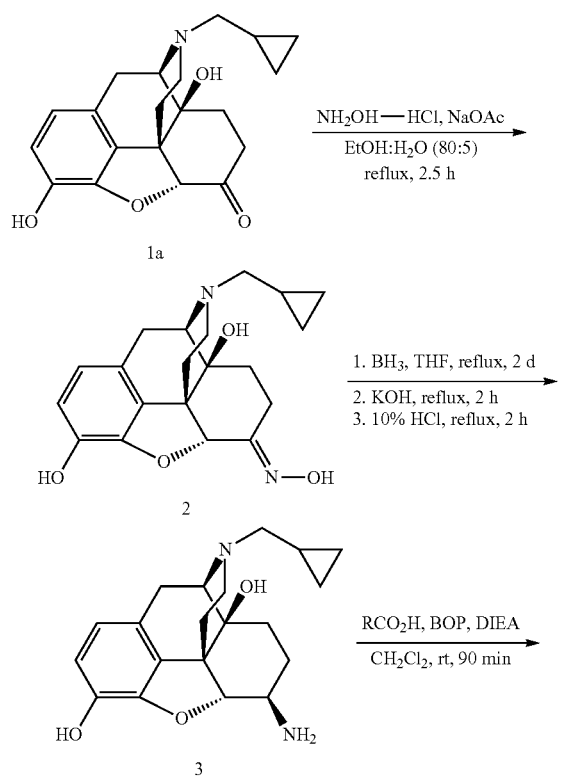

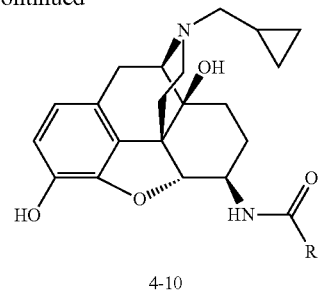

4-10

4: R = p-Methylphenyl
5: R = p-Trifluoromethylphenyl
6: R = p-Bromophenyl
7: R = p-Iodophenyl
8: R = p-t-Butylphenyl
9: R = 3,4-Dichlorophenyl
10: R = p-Chlorophenyl

Example 1

Naltrexone Oxime (2)

Naltrexone 1 (500 mg, 1.46 mmol), NH$_2$OH—HCl (147 mg) and NaOAc (294 mg) were dissolved in absolute ethanol (8 mL) and the mixture was heated at reflux for 2.5 h and then concentrated to dryness. Water (20 mL) was added and the mixture was made basic with K$_2$CO$_3$ and extracted with CHCl$_3$. The CHCl$_3$ extract was washed with brine, dried over Na$_2$SO$_4$, filtered and concentrated to give a white solid (463 mg, 89%): ESI-MS m/z 357 (MH$^+$). $^1$H NMR (CDCl$_3$) δ 6.75 (d, J=8.2 Hz, 1H), 6.61 (d, J=8.2 Hz, 1H), 5.0 (s, 1H), 3.15 (m, 2H), 2.65-1.3 (m, 10H), 0.86 (m, 1H), 0.56 (m, 2H), 0.2 (m, 2H).

Example 2

6-α-Naltrexamine (3a). And 6-β-Naltrexamine (3b)

Naltrexone oxime (5.83 g, 16.3 mmol) was dissolved in THF (40 mL) and transferred by cannula over 10 min to a solution of BH$_3$:THF (300 mL, 300 mmol, 1 M solution in THF) held at 10° C. A white precipitate formed and then slowly dissolved as the reaction was heated at reflux for 48 h. The solution was cooled to room temperature and water (10 mL) and 1 N KOH (200 mL) was added slowly. The solution was then reheated at reflux for 2 h. The pH was reduced to 2.5 with 10% HCl (225 mL) and the solution was heated at reflux for additional 2 h. The THF was removed under vacuum and the aqueous solution was made basic (pH 8-9) with K$_2$CO$_3$. The mixture was extracted with CHCl$_3$ (4×150 mL) and the extract was dried over Na$_2$SO$_4$, filtered and concentrated. The resulting oil was purified by chromatography on SiO$_2$ (26×60 cm, elution with CH$_3$CN/MeOH/NH$_4$OH, 25:5:1, v:v) providing 3b (beta diastereomer) (2.14 g, 38%) as a white-yellow solid: R$_f$=0.2; $^1$H NMR (300 MHz, CDCl$_3$ with 2 drops of CD$_3$OD) δ6.61 (d, J=8.1 Hz, 1H), 6.49 (d, J=8.1 Hz, 1H), 4.17 (d, J=7.5 Hz, 1H), 3.39-0.45 (20H); MS m/z 343 (MH$^+$). An additional 0.64 g (12%) of material consisting of a mixture of the α- and β-diastereomers was isolated. Repeated chromatography gave an analytical sample of the α-diastereomer, compound 3a: R$_f$=0.16; $^1$H NMR δ6.65 (d, J=8.1 Hz, 1H), 6.46 (d, J=8.1 Hz, 1H), 4.50 (d, J=3.0 Hz, 1H), 3.34 (dt, J=3.9, 12.6 Hz, 1H), 3.04 (t, J=6.6 Hz, 1H), 2.95 (s, 1H), 2.63-0.29 (17H); MS m/z 343 (MH$^+$).

Example 3

6-α-N-Methylnaltrexamine (3c) and 6-β-N-Methylnaltrexamine (3d)

Synthesis of 6-α-N-methylnaltrexamine (3c) and 6-β-N-methylnaltrexamine (3d) was done as follows: To a mixture of naltrexone (100 mg, 0.29 mmol) and methylamine (2.0 M solution in methanol, 1.5 mL, 2.9 mmol) was added methanolic solution of $NaCNBH_3$ (12 mg, 0.18 mmol). The pH was adjusted to 7 with concentrated HCl. The mixture was then stirred at room temperature for 3 days. The solution was acidified to pH 1 with concentrated HCl and the solvent was removed in vacuo. The resultant residue was dissolved in water and extracted with chloroform to remove water insoluble material. The pH of the aqueous solution was adjusted to 9 with sodium carbonate, extracted with chloroform, dried over $Na_2SO_4$, filtered and chloroform was removed in vacuo. The resultant crude product was purified by flash chromatography ($EtOAc/MeOH/NH_4OH$, 10:8:0.3, v:v) to give the a diastereomer, 3c (36.9 mg) and the β diastereomer, 3d (35.2 mg) as white solids.

6-α-N-Methylnaltrexamine 3c: ESI/MS: m/z=357 ($MH^+$), 355 ($MH^-$); $R_f$=0.18; $^1H$ NMR ($CDCl_3$) δ 6.67 (d, J=8.0 Hz, 1H), 6.48 (d, J=8.0 Hz, 1H), 4.75 (d, J=3.5 Hz, 1H), 3.14-3.0 (m, 2H), 2.64 (m, 1H), 2.58 (S, 3H), 2.53-1.38 (m, 11H), 0.84 (m, 1H), 0.53 (m, 2H), 0.12 (m, 2H).

6-β-N-Methylnaltrexamine, 3d: ESI/MS: m/z=357 ($MH^+$), 355 ($MH^-$); $R_f$=0.28; $^1H$ NMR ($CDCl_3$) δ 6.64 (d, J=8.1 Hz, 1H), 6.53 (d, J=8.1 Hz, 1H), 4.51 (d, J=7.6 Hz, 1H), 3.05-3.0 (m, 2H), 2.64-2.56 (m, 3H), 2.48 (S, 3H), 2.36-1.39 (m, 9H), 0.83 (m, 1H), 0.51 (m, 2H), 0.11 (m, 2H).

Example 4

General Procedure for the Amidation of Naltrexamine with an Acid Chloride

Naltrexamine (104 mg, 0.3 mmol) was dissolved in $CH_2Cl_2$ (4 mL) and $NEt_3$ (0.13 mL, 0.93 mmol) and substituted benzoyl chloride (0.73 mmol) was added. The solution was stirred for 2 h at room temperature and concentrated to dryness. The residue was filtered through a column of $SiO_2$ ($CH_2Cl_2/MeOH$, 20:1, v:v). The resulting solid was dissolved in anhydrous methanol (3 mL) and $K_2CO_3$ (300 mg) was added. The mixture was stirred at room temperature for 12 h, concentrated and purified by $SiO_2$ chromatography.

Example 5

General Procedure for the Amidation of Naltrexamine with a Carboxylic Acid

Naltrexamine (100 mg, 0.29 mmol), substituted benzoic acid (0.58 mmol) and BOP (258 mg, 0.58 mmol) were dissolved in $CH_2Cl_2$ (3 mL). To this solution, $Pr_2EtN$ (0.15 mL, 0.88 mmol) was added and the mixture was stirred at room temperature for 2 h. The solution was concentrated and filtered through a short column of $SiO_2$ (eluted with EtOAc) providing a white material. This product was dissolved in MeOH (3 mL) and $K_2CO_3$ (300 mg) was then added. The mixture was stirred at room temperature for 3 h and concentrated to dryness. The residue was purified by $SiO_2$ chromatography ($CH_2Cl_2/MeOH$, 20:1, v:v) to provide the target compound.

Example 6

6-β-(4'-Methyl)benzamido-14-hydroxy-17-(cyclopropylmethyl) nordesmorphine (4)

Compound 4 was synthesized according to the general procedure described above; β-Naltrexamine (100 mg, 0.29 mmol), p-toluoyl chloride (0.09 mL, 0.7 mmol) and triethylamine (0.13 mL, 0.91 mmol) combined in dichloromethane followed by basic hydrolysis with $K_2CO_3$ gave the title compound as a white solid (107 mg, 79%). mp=207.6° C.; $R_f$=0.04 ($CHCl_3/MeOH$, 20:1, v:v); ESI/MS m/z=461 ($MH^+$); $^1H$ NMR ($CDCl_3/CD_3OD$, 9:1) δ 7.68 (d, J=8.1 Hz, 2H), 7.23 (d, J=8.1 Hz, 2H), 6.67 (d, J=8.1 Hz, 2H), 6.51 (d, J=8.1 Hz, 1H), 4.40 (d, J=6.6 Hz, 1H), 4.15-4.05 (m, 1H), 3.09-2.96 (m, 2H), 2.60 (m, 2H), 2.34 (s, 3H), 2.12-1.40 (m, 6H) 0.50 (m, 2H), 0.09 (m, 2H); $^{13}C$ NMR ($CDCl_3/CD_3OD$, 9:1) δ 168.1, 142.8, 142.1, 139.9, 131.0, 130.4, 128.9, 128.1, 127.3, 126.7, 123.7, 118.6, 93.0, 70.4, 62.3, 61.9, 59.0, 49.6, 48.7, 47.3, 22.6, 9.3, 3.9, 3.6; HRMS calcd for $C_{28}H_{33}N_2O_4$ 461.2440. found 461.2440.

Example 7

6-β-(4'-Methyl)benzamido-14-hydroxy-17-(cyclopropylmethyl) nordesmorphine oxalate (4-oxalate)

Compound 4 (50 mg) was converted to its oxalic salt using 1 equivalent oxalic acid in methanol (3 mL). Solubility in $H_2O$ is 2 mg/mL.

Example 8

6-β-(4'-Trifluoromethyl)benzamido-14-hydroxy-17-(cyclopropylmethyl)nordesmorphine Compound (5). was synthesized according to the general procedure described above; β-Naltrexamine (100 mg, 0.29 mmol), 4-(trifluoromethyl)benzoyl chloride (0.12 mL, 0.73 mmol) and triethylamine (0.12 mL, 0.88 mmol) combined in dichloromethane followed by basic hydrolysis with $K_2CO_3$ gave the title compound as a white solid (117 mg, 78% yield). $R_f$=0.11; mp=157.5° C.; ESI/MS m/z=515 ($MH^+$); $^1H$ NMR ($CDCl_3$) δ 7.92 (d, J=8.4 Hz, 2H), 7.63 (d, J=8.4 Hz, 2H), 6.67 (d, J=7.8 Hz, 2H), 6.53 (d, J=7.8 Hz, 1H), 4.6 (d, J=5.4 Hz, 1H), 4.16-4.13 (m, 1H), 3.15-1.44 (m, 11H), 0.54 (m, 2H), 0.13 (m, 2H); $^{13}C$ NMR ($CDCl_3$) δ 166.2, 142.6, 139.4, 137.4, 130.5, 128.1, 127.3, 125.4, 125.1, 124.3 121.8, 119.4, 118.1, 92.6, 70.4, 62.3, 61.9, 59.2, 51.3, 50.8, 47.2, 22.6, 9.3, 3.9; HRMS calcd for $C_{28}H_{30}F_3N_2O_4$ 515.2158. found 515.2137.

Example 9

6-β-(4'-Trimethylfluoro)benzamido-14-hydroxy-17-(cyclopropylmethyl)nordesmorphine-oxalate (5-oxalate)

The amide product was converted to its oxalic salt using one equivalent of oxalic acid dihydrate in methanol. Solubility: 1 mg/mL in $H_2O$.

Example 10

6-β-(4'-Bromo)benzamido-14-hydroxy-17-(cyclopropylmethyl) nordesmorphine (6)

Compound 6 was synthesized according to the general procedure described above; β-Naltrexamine (70 mg, 0.2 mmol), p-bromobenzoic acid (62 mg, 0.31 mmol), BOP (137 mg, 0.31 mmol) and N,N-diisopropylethylamine (0.11 mL, 0.61 mmol) combined in dichloromethane (2 mL) followed by basic hydrolysis with $K_2CO_3$ gave the title compound as a white foam (101 mg, 94%). $R_f$=0.02; ESI/MS m/z=525 ($MH^+$); $^1H$ NMR ($CDCl_3$) δ 7.71 (d, J=8.1 Hz, 2H), 7.51 (d, J=8.1 Hz, 2H), 6.73 (d, J=7.8 Hz, 2H), 6.52 (d, J=7.8 Hz, 1H), 4.56 (d, J=6.0 Hz, 1H), 4.16-4.13 (m, 1H), 3.12-1.46 (m, 11H), 0.52 (m, 2H), 0.12 (m, 2H); $^{13}C$ NMR ($CDCl_3$) δ 166.1, 143.2, 139.9, 133.4, 132.5, 131.7, 130.5, 129.1, 128.2, 125.4, 124.1, 121.8, 119.4, 118.1, 92.6, 70.2, 62.4, 61.9, 59.3, 47.1, 37.6, 36.8, 36.7, 35.9, 9.3, 3.9; HRMS calcd for $C_{27}H_{30}BrN_2O_4$ 525.1389. found 525.1382.

Example 11

6-β-(4'-Bromo)benzamido-14-hydroxy-17-(cyclopropylmethyl) nordesmorphine-oxalate (6-oxalate)

The amide product was converted to its oxalic salt using one equivalent of oxalic acid dihydrate in methanol. Solubility: 0.2 mg/mL in $H_2O$.

Example 12

6-β-(4'-Iodo)benzamido-14-hydroxy-17-(cyclopropylmethyl)nordesmorphine (7)

Compound 7 was synthesized according to the general procedure described above; β-Naltrexamine (50 mg, 0.20 mmol), p-iodobenzoic acid (55 mg, 0.22 mmol), BOP (97 mg, 0.22 mmol) and N,N-diisopropylethylamine (0.08 mL, 0.44 mmol) combined in dichloromethane (2 mL) followed by basic hydrolysis with $K_2CO_3$ gave the title compound as a white foam (83 mg, 97%). $R_f$=0.05; ESI/MS m/z=572.9 ($MH^+$); $^1H$ NMR ($CDCl_3$) δ 7.68 (d, J=8.1 Hz, 2H), 7.55 (d, J=8.1 Hz, 2H), 6.72 (d, J=8.1 Hz, 2H), 6.51 (d, J=8.1 Hz, 1H), 4.56 (d, J=6 Hz, 1H), 4.11-4.08 (m, 1H), 3.1-1.44 (m, 11H), 0.51 (m, 2H), 0.11 (m, 2H); $^{13}C$ NMR ($CDCl_3$) δ 166.4, 143.2, 140, 137.8, 137.1, 133.9, 130.5, 129.1, 128.2, 124, 119.4, 118.1, 92.3, 70.2, 64.4, 62.0, 59.2, 47.2, 37.6, 36.8, 36.7, 35.9, 9.3, 3.9; HRMS calcd for $C_{27}H_{30}IN_2O_4$ 573.1250. found 573.1237.

Example 13

6-β-(4'-Iodo)benzamido-14-hydroxy-17-(cyclopropylmethyl)nordesmorphine-oxalate (7-oxalate)

The amide product was converted to its oxalic salt using one equivalent of oxalic acid dihydrate in methanol. Solubility: 0.2 mg/mL in $H_2O$.

Example 14

6-(4'-t-Butyl)benzamido-14-hydroxy-17-(cyclopropylmethyl)nordesmorphine (8)

Compound 8 was synthesized according to the general procedure described above; β-Naltrexamine (50 mg, 0.15 mmol), 4-t-butylbenzoyl chloride (0.14 mL, 0.7 mmol) and $NEt_3$ (0.07 mL, 0.88 mmol) combined in dichloromethane (2 mL) followed by basic hydrolysis with $K_2CO_3$ gave the title compound as a white solid (47 mg, 64%). $R_f$=0.09; mp=151.1° C.; ESI/MS m/z=503 ($MH^+$), 501 ($MH^-$); $^1H$ NMR ($CDCl_3$) δ 7.75 (d, J=8.4 Hz, 2H), 7.40 (d, J=8.4 Hz, 2H), 6.72 (d, J=7.8 Hz, 2H), 6.55 (d, J=7.8 Hz, 1H), 4.53 (d, J=5.7 Hz, 1H), 4.21-4.18 (m, 1H), 3.14-1.44 (m, 11H), 0.54 (m, 2H), 0.13 (m, 2H); $^{13}C$ NMR ($CDCl_3$) δ 167.2, 143.1, 139.5, 137.4, 131.4, 130.6, 127.3, 126.6, 125.5, 124.5, 119.4, 118.0, 93.2, 70.1, 62.4, 62, 59.3, 49.6, 47.2, 34.2, 31.3, 31, 9.3, 3.9; HRMS calcd for $C_{31}H_{39}N_2O_4$ 503.2910. found 503.2893.

Example 15

6-β-(4'-t-Butyl)benzamido-14-hydroxy-17-(cyclopropylmethyl)nordesmorphine-oxalate (8-oxalate)

The amide product was converted to its oxalic salt using one equivalent of oxalic acid dihydrate in methanol. Solubility: 6 mg/mL in $H_2O$.

Example 16

6-β-(3',4'-Dichloro)benzamido-14-hydroxy-17-(cyclopropylmethyl)nordesmorphine (9)

Compound 9 was prepared according to the general procedure described above, β-Naltrexamine (100 mg, 0.29 mmol), 3,4-dichlorobenzoyl chloride (153 mg, 0.73 mmol) and $Et_3N$ (0.15 mL, 0.1 mmol) combined for 2 hr followed by basic hydrolysis with $K_2CO_3$ (1 g) gave the title compound as a white solid (138 mg, 92%). mp=108.6° C.; $R_f$=0.36 ($CH_2Cl_2$/MeOH, 10:1, v:v); ESI/MS m/z=516 ($MH^+$); $^1H$ NMR ($CDCl_3$) δ 7.93 (d, J=1.8 Hz, 1H); 7.67-7.64 (m, 2H), 7.42 (d, J=8.4 Hz, 1H); 6.6 (d, J=8.1 Hz, 1H); 6.51 (d, J=8.1 Hz, 1H), 4.71 (d, J=6.3 Hz, 1H), 3.99-3.93 (m, 1H); $^{13}C$ NMR ($CDCl_3$) δ 164.7, 142.2, 139.1, 135.6, 133.8, 132.6, 130.4, 130.2, 129.2, 126.2, 124.5, 119.3, 117.5, 92.3, 70.3, 62.2, 59.3, 51.2, 47.4, 43.9, 31.6, 29.4, 23.5, 22.7, 9.5, 4.1, 4; HRMS calcd for $C_{27}H_{28}Cl_2N_2O_4$ 515.1505. found 515.1498.

Example 17

6-β-(3',4'-Dichloro)benzamido-14-hydroxy-17-(cyclopropylmethyl)nordesmorphine hydrochloride (9.HCl)

The amide product 9 was dissolved in ether and hydrochloride gas was bubbled to the solution. The precipitated hydrochloride salt was collected by filtration. Solubility: 1 mg/mL in $H_2O$.

Example 18

6-β-(4'-Chloro)benzamido-14-hydroxy-17-(cyclopropylmethyl)nordesmorphine (10)

Compound 10 was synthesized according to the general procedure described above; combining β-naltrexamine (100 mg, 0.29 mmol), 4-chlorobenzoic acid (68 mg, 0.44 mmol), BOP (190 mg, 0.44 mmol) and $Pr_2EtN$ (0.16 mL, 0.87 mmol) followed by basic hydrolysis with $K_2CO_3$ gave the title compound as a white solid (28 mg, 20%). mp=188.8° C.; $R_f$=0.06 ($CHCl_3$/MeOH, 30:1, v:v); ESI/MS m/z=481 ($MH^+$); $^1H$ NMR ($CDCl_3/CD_3OD$, 9:1, v:v) δ 7.77 (d, J=7.8 Hz, 2H), 7.4 (d, J=7.8 Hz, 2H), 6.7 (d, J=8.4 Hz, 2H), 6.51 (d, J=8.4 Hz, 1H), 4.4 (d, J=6.6 Hz, 1H), 4.15-4.05 (m, 1H), 3.1-1.35 (m, 11H), 0.5 (m, 2H), 0.1 (m, 2H); $^{13}C$ NMR ($CDCl_3/CD_3OD$, 9:1, v:v) δ 166.8, 142.6, 139.7, 137.6, 132.3, 130.2, 128.5, 128.4, 123.7, 118.9, 118.3, 92.7, 70.5, 62.1, 59, 50.8, 47.3, 43.8, 31.2, 29.4, 23.9, 22.5, 9.3, 3.9, 3.7; HRMS calcd for $C_{27}H_{29}ClN_2O_4$ 481.1894. found 481.1879.

Example 19

6-β-(4'-Chloro)benzamido-14-hydroxy-17-(cyclopropylmethyl)nordesmorphine hydrochloride (10.HCl)

The amide product 10 was dissolved in ether and hydrochloride gas was bubbled to the solution. The precipitated hydrochloride salt was collected by filtration. Solubility: 18 mg/mL in $H_2O$.

Example 20

6-β-(3'-Cyano)benzamido-14-hydroxy-17-(cyclopropylmethyl)nordesmorphine (11)

Compound 11 was synthesized according to the general procedure described above; β-Naltrexamine (100 mg, 0.29 mmol), m-cyanobenzoic acid (65 mg, 0.44 mmol), BOP (195 mg, 0.44 mmol) and N,N-diisopropylethylamine (0.15 mL, 0.88 mmol) combined in dichloromethane (3 mL) followed by basic hydrolysis with $K_2CO_3$ gave the title compound as a white foam (136 mg, 99%). $R_f$=0.02; ESI/MS: m/z=472 (MH$^+$), 494 (MNa$^+$), 470 (MH$^-$), 506 (MCl$^-$); $^1$H NMR (CDCl$_3$) δ 8.16 (s, 1H), 8.11 (d, J=7.8 Hz, 1H), 7.91 (d, J=9.1 Hz, NH, 1H), 7.76 (d, J=7.8 Hz, 1H), 7.56 (t, J=7.8 Hz, 1H), 6.73 (d, J=8.1 Hz, 1H), 6.55 (d, J=8.1 Hz, 1H), 4.57 (d, J=4.9 Hz, 1H), 4.25 (m, 1H), 3.17-3.02 (m, 2H), 2.79-1.48 (m, 11H), 0.88 (m, 1H), 0.55 (m, 2H), 0.13 (m, 2H).

Example 21

6-(3'-N-Hydroxycarbamimidoyl)benzamido-14-hydroxy-17-(cyclopropylmethyl)nordesmorphine (12)

Hydroxylamine hydrochloride (74 mg, 1.1 mmol) was suspended in anhydrous DMF (1.2 mL). KOt-Bu (119 mg, 1.06 mmol) was added and the mixture was stirred at room temperature for 1 h. To this solution, the cyano compound 11 (50 mg, 0.11 mmol) was added and the reaction mixture was stirred at room temperature overnight. Solvent was evaporated to dryness. The white residue was dissolved in $CH_2Cl_2$ and water, extracted with dichloromethane (5×5 mL). The organic extract was washed with brine, dried over $Na_2SO_4$, filtered and concentrated to dryness to provide 49 mg, 90% yield of the product as a white solid. $R_f$=0.12; ESI/MS: m/z=505 (MH$^+$), $^1$H NMR (CDCl$_3$) δ 8.01 (s, 1H), 7.6 (m, 1H), 7.32 (m, 1H), 6.71 (m, 1H), 6.56 (m, 1H), 6.53 (m, 1H), 5.18 (s, 1H), 4.66 (d, J=5.1 Hz, 1H), 4.05 (m, 1H), 3.1-1.37 (m, 13H), 0.87 (m, 1H), 0.18 (m, 2H), 0.09 (m, 2H).

Scheme 2. Synthesis of 6-N-methylnaltrexamides.

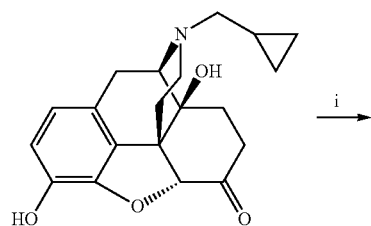

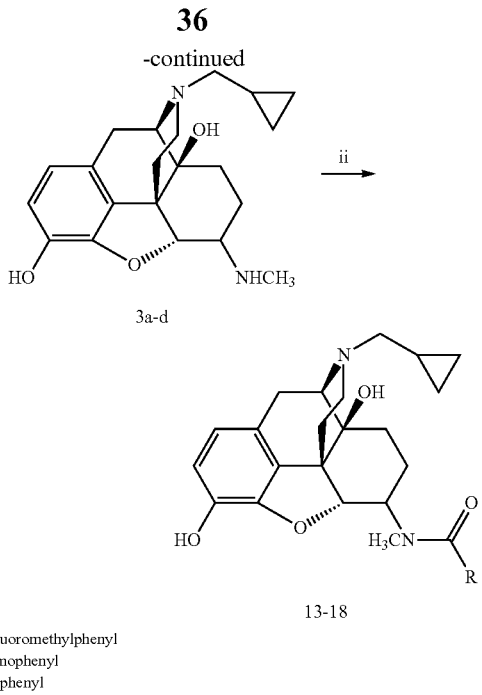

3a-d 13-18

13: R = p-Trifluoromethylphenyl
14: R = p-Bromophenyl
15: R = p-Iodophenyl
16: R = p-t-Butylphenyl
17: R = p-Chlorophenyl
18: R = 3,4-Dichlorophenyl
i) Methylamine/MeOH, NaCNBH$_3$;
ii) RCO$_2$H, BOP, DIEA, CH$_2$Cl$_2$, 90 min. or RCOCl, Et$_3$N, CH$_2$Cl$_2$, 2 h.

Example 22

6-α-(4'-Trifluoromethyl)-N-methylbenzamido-14-hydroxy-17-(cyclopropylmethyl)nordesmorphine (13a)

The general procedure is illustrated by the following. 6-α-N-Methylnaltrexamine (30 mg, 0.08 mmol) was dissolved in $CH_2Cl_2$ (1 mL) and NEt$_3$ (0.03 mL, 0.25 mmol) and 4-(trifluoromethyl)benzoyl chloride (0.03 mL, 0.21 mmol) was added. The solution was stirred for 2 h at room temperature and concentrated to dryness. The crude product was dissolved in anhydrous methanol (3 mL) and $K_2CO_3$ (300 mg) was added. The mixture was stirred at room temperature for 12 h, concentrated and purified by $SiO_2$ chromatography (20:1 $CH_2Cl_2$:MeOH) to afford 25 mg, 57% as a white powder. $R_f$=0.28; ESI/MS: m/z=529 (MH$^+$), 551 (MNa$^+$), 527 (MH$^-$); $^1$H NMR (CDCl$_3$) δ: 7.67 (d, J=7.3 Hz, 2H), 7.55 (d, J=7.3 Hz, 2H), 6.70 (d, J=7.6 Hz, 1H), 6.54 (d, J=7.6 Hz, 1H), 5.16 (m, 1H), 5.07 (s, 1H), 3.51-1.25 (m, 14H), 0.86 (m, 1H), 0.53 (m, 2H), 0.09 (m, 2H); $^{13}$C NMR (CDCl$_3$) δ: 170.6, 145.7, 140.8, 137.4, 131.6, 131.4, 131.3, 127.5, 127.3, 126.7, 126.6, 125.7, 125.1, 122.9, 119.4, 117.2, 91.9, 69.5, 62.5, 60.0, 50.9, 48.2, 43.2, 35.0, 33.7, 30.4, 29.9, 23.1, 18.8, 9.6, 4.3, 4.2, 4.2, 4.1

Example 23

6-α-(4'-Trifluoromethyl)-N-methylbenzamido-14-hydroxy-17-(cyclopropylmethyl)nordesmorphine oxalate (13a—Oxalate)

The amide product was converted to its oxalic salt using one equivalent of oxalic acid dihydrate in methanol. Solubility: 10 mg/mL in $H_2O$.

Example 24

6-β-(4'-Trifluoromethyl)-N-methylbenzamido-14-hydroxy-17-(cyclopropylmethyl)nordesmorphine (13b)

Compound 13b was synthesized according to the general procedure described for compound 13a. 6-β-N-Methylnaltrexamine (42 mg, 0.12 mmol), NEt$_3$ (0.05 mL, 0.42 mmol) and 4-(trifluoromethyl)benzoyl chloride (0.03 mL, 0.21 mmol) were combined in CH$_2$Cl$_2$ (2 mL). After basic hydrolysis with K$_2$CO$_3$, the crude product was purified by SiO$_2$ chromatography (CH$_2$Cl$_2$:MeOH, 20:1, v:v) to afford 41.3 mg, 56% as a white powder. R$_f$=0.08; ESI/MS m/z=529 (MH$^+$), 551 (MNa$^+$), 527 (MH$^-$); $^1$H NMR (CDCl$_3$): 7.53 (d, J=8.1 Hz, 2H), 7.47 (d, J=8.1 Hz, 2H), 6.56 (d, J=8.2 Hz, 1H), 6.44 (d, J=8.2 Hz, 1H), 4.69 (d, J=7.9 Hz, 1H), 3.14 (s, 3H), 3.09-1.35 (m, 14H), 0.86 (m, 1H), 0.52 (m, 2H), 0.1 (m, 2H).

Example 25

6-β-(4'-Trifluoromethyl)-N-methylbenzamido-14-hydroxy-17-(cyclopropylmethyl)nordesmorphine oxalate (13b—Oxalate)

The amide product 13b was converted to its oxalic salt using one equivalent of oxalic acid dihydrate in methanol. Solubility: 4.7 mg/mL in H$_2$O.

Example 26

6-α-(4'-Bromo)-N-methylbenzamido-14-hydroxy-17-(cyclopropylmethyl)nordesmorphine (14a)

6-α-N-Methylnaltrexamine (30 mg, 0.08 mmol), p-bromobenzoic acid (25 mg, 0.13 mmol) and BOP (56 mg, 0.13 mmol) were dissolved in CH$_2$Cl$_2$ (2 mL). To this solution, Pr$_2$EtN (0.05 mL, 0.39 mmol) was added and the mixture was stirred at room temperature for 2 h. The solution was concentrated to dryness. The crude product was dissolved in MeOH (3 mL) and K$_2$CO$_3$ (300 mg) was then added. The mixture was stirred at room temperature overnight. The salt was filtered off and solvent was evaporated to dryness. The residue was purified by SiO$_2$ chromatography (CH$_2$Cl$_2$/MeOH, 20:1, v:v) to provide 25 mg, 55% of the target compound as a white powder. R$_f$=0.09; ESI/MS m/z=539 (MH$^+$), 537 (MH$^-$); $^1$H NMR (CDCl$_3$) δ: 7.54 (d, J=7.8 Hz, 2H), 7.29 (d, J=7.8 Hz, 2H), 6.71 (d, J=8.1 Hz, 1H), 6.52 (d, J=8.1 Hz, 1H), 5.11 (m, 1H), 5.05 (s, 1H), 3.12-1.37 (m, 14H), 0.52 (m, 2H), 0.08 (m, 2H); $^{13}$C NMR (CDCl$_3$) δ: 171.0, 145.7, 137.7, 136.1, 132.0, 131.8, 129.0, 126.3, 126.2, 123.8, 119.3, 117.3, 91.8, 69.5, 59.9, 50.9, 48.2, 43.2, 37.0, 35.1, 33.7, 30.4, 29.9, 23.0, 18.8, 9.6, 4.3, 4.2, 4.0.

Example 27

6-α-(4'-Bromo)-N-methylbenzamido-14-hydroxy-17-(cyclopropylmethyl)nordesmorphine oxalate (14a—Oxalate)

The amide product was converted to its oxalic salt using one equivalent of oxalic acid dihydrate in methanol. Solubility: 6.7 mg/mL in H$_2$O.

Example 28

6-β-(4'-Bromo)-N-methylbenzamido-14-hydroxy-17-(cyclopropylmethyl)nordesmorphine (14b)

The procedure followed the method of compound 14a. β-N-Methylnaltrexamine (50 mg, 0.14 mmol), p-bromobenzoic acid (42 mg, 0.21 mmol), BOP (93 mg, 0.21 mmol) and Pr$_2$EtN (0.04 mL, 0.21 mmol) were combined in CH$_2$Cl$_2$ (2 mL). Basic hydrolysis followed by purification by SiO$_2$ chromatography (CH$_2$Cl$_2$/MeOH, 20:1, v:v) provided 56 mg, 75% of the target compound as a white powder. R$_f$=0.16; ESI/MS m/z=539 (MH$^+$), 537 (MH$^-$); $^1$H NMR (CDCl$_3$) δ: 7.45 (d, J=8.1 Hz, 2H), 7.35 (d, J=8.1 Hz, 2H), 6.72 (d, J=8.1 Hz, 1H), 6.43 (d, J=8.1 Hz, 1H), 4.69 (d, J=7.9 Hz, 1H), 3.1 (s, 3H), 2.99-1.42 (m, 14H), 0.81 (m, 1H), 0.51 (m, 2H), 0.1 (m, 2H).

Example 29

6-β-(4'-Bromo)-N-methylbenzamido-14-hydroxy-17-(cyclopropylmethyl)nordesmorphine Oxalate (14b. Oxalate)

The amide product 14b was converted to its oxalic salt using one equivalent of oxalic acid dihydrate in methanol. Solubility: 20 mg/mL in H$_2$O.

Example 30

6-α-(4'-Iodo)-N-methylbenzamido-14-hydroxy-17-(cyclopropylmethyl)nordesmorphine (15a)

The procedure followed the method of compound 14a. 6-α-N-Methylnaltrexamine (30 mg, 0.08 mmol), p-iodobenzoic acid (31.3 mg, 0.13 mmol) and BOP (56 mg, 0.13 mmol) were combined in CH$_2$Cl$_2$ (2 mL). The product was purified by SiO$_2$ chromatography (CH$_2$Cl$_2$/MeOH, 20:1, v:v) to provide 29 mg, 59% of the target compound as thick oil. ESI/MS m/z=587 (MH$^+$), 585 (MH$^-$); $^1$H NMR (CDCl$_3$) δ 7.75 (d, J=7.8 Hz, 2H), 7.17 (d, J=7.8 Hz, 2H), 6.71 (d, J=8.1 Hz, 1H), 6.53 (d, J=8.1 Hz, 1H), 5.11 (m, 1H), 5.05 (s, 1H), 3.11-1.55 (m, 14H), 0.52 (m, 2H), 0.11 (m, 2H); $^{13}$C NMR (CDCl$_3$) δ 171, 137.8, 136.8, 129, 119.3, 117.2, 95.6, 69.5, 59.9, 50.9, 48.2, 43.2, 37.1, 32.1, 29.9, 29.6, 23.1, 14.3, 9.6, 4.2, 4.

Example 31

6-α-(4'-Iodo)-N-methylbenzamido-14-hydroxy-17-(cyclopropylmethyl)nordesmorphine oxalate (15a—Oxalate)

The amide product 15a was converted to its oxalic salt using one equivalent of oxalic acid dihydrate in methanol. Solubility: 5 mg/mL in H$_2$O.

Example 32

6-β-(4'-Iodo)-N-methylbenzamido-14-hydroxy-17-(cyclopropylmethyl)nordesmorphine (15b)

The procedure followed the method of compound 14a. β-N-Methylnaltrexamine (40 mg, 0.11 mmol), p-iodobenzoic acid (42 mg, 0.17 mmol), BOP (75 mg, 0.17 mmol) and N,N-diisopropylethylamine (0.03 mL, 0.17) were combined in CH$_2$Cl$_2$ (2 mL). After basic hydrolysis, the crude product was purified by SiO$_2$ chromatography (CH$_2$Cl$_2$/MeOH, 20:1, v:v) to provide 46 mg, 72% of the target compound as a thick oil. ESI/MS m/z=587 (MH$^+$), 585 (MH$^-$); $^1$H NMR (CDCl$_3$): 7.62 (d, J=7.9 Hz, 2H), 7.18 (d, J=7.9 Hz, 2H), 6.7 (d, J=8.1 Hz, 1H), 6.46 (d, J=8.1 Hz, 1H), 4.68 (d, J=7.8 Hz, 1H), 3.1 (s, 3H), 2.99-1.42 (m, 14H), 0.82 (m, 1H), 0.52 (m, 2H), 0.11 (m, 2H).

Example 33

6-β-(4'-Iodo)-N-methylbenzamido-14-hydroxy-17-(cyclopropylmethyl)nordesmorphine oxalate (15b—Oxalate)

The amide product, 15b was converted to its oxalic salt using one equivalent of oxalic acid dihydrate in methanol. Solubility: 20 mg/mL in H$_2$O.

Example 34

6-α-(4'-t-Butyl)-N-methylbenzamido-14-hydroxy-17-(cyclopropylmethyl)nordesmorphine (16a)

The general method of compound 13a was used: α-N-Methylnaltrexamine (30 mg, 0.08 mmol) in CH$_2$Cl$_2$ (1 mL) and NEt$_3$ (0.03 mL, 0.25 mmol) and 4-tert-butylbenzoyl chloride (0.04 mL, 0.20 mmol) was added. The product was purified by SiO$_2$ chromatography (CH$_2$Cl$_2$:MeOH, 20:1, v:v) to afford 37 mg, 85% as a white powder. R$_f$=0.08; mp=274.8° C.; ESI/MS m/z=517 (MH$^+$), 539 (MNa$^+$), 515 (MH$^-$); $^1$H NMR (CDCl$_3$) δ 7.39-7.26 (m, 4H), 6.70 (d, J=7.7 Hz, 1H), 6.52 (d, J=7.7 Hz, 1H), 5.11 (m, 2H), 3.11-1.20 (m, 25H), 0.86 (m, 1H), 0.53 (m, 2H), 0.11 (m, 2H); $^{13}$C NMR (CDCl$_3$) δ 173.1, 152.7, 145.8, 137.6, 134.3, 127.1, 126.9, 126.8, 126.2, 125.4, 119.2, 117.2, 92.1, 69.5, 62.5, 59.9, 50.9, 48.2, 43.3, 35.2, 35.1, 33.7, 31.6, 31.5, 31.4, 30.4, 29.9, 23.1, 19.0, 9.6, 4.2, 4.0.

Example 35

6-α-(4'-t-Butyl)-N-methylbenzamido-14-hydroxy-17-(cyclopropylmethyl)nordesmorphine oxalate (16a—Oxalate)

The amide product 16a was converted to its oxalic salt using one equivalent of oxalic acid dihydrate in methanol. Solubility: 3.3 mg/mL in H$_2$O.

Example 36

6-β-(4'-t-Butyl)-N-methylbenzamido-14-hydroxy-17-(cyclopropylmethyl)nordesmorphine (16b)

The general method of compound 13a was used: β-N-Methylnaltrexamine (34 mg, 0.1 mmol), 4-tert-butylbenzoyl chloride (0.05 mL, 0.23 mmol) and NEt$_3$ (0.04 mL, 0.28 mmol) were combined in CH$_2$Cl$_2$ (2 mL). After basic hydrolysis, the crude product was purified by SiO$_2$ chromatography (CH$_2$Cl$_2$:MeOH, 20:1, v:v) to afford 39 mg, 80% as a white powder. R$_f$=0.16, ESI/MS m/z=517 (MH$^+$), 539 (MNa$^+$), 515 (MH$^-$); $^1$H NMR (CDCl$_3$) δ 7.41-7.36 (m, 4H), 6.5 (d, J=7.8 Hz, 1H), 6.4 (d, J=7.8 Hz, 1H), 4.64 (d, J=7.5 Hz, 1H), 3.11 (s, 3H), 3.07-1.15 (m, 23H), 0.86 (m, 1H), 0.53 (m, 2H), 0.11 (m, 2H).

Example 37

6-β-(4'-t-Butyl)-N-methylbenzamido-14-hydroxy-17-(cyclopropylmethyl)nordesmorphine oxalate (16b—Oxalate)

The amide product 16b was converted to its oxalic salt using one equivalent of oxalic acid dihydrate in methanol. Solubility: 6.7 mg/mL in H$_2$O.

Example 38

6-α-(4'-Chloro)-N-methylbenzamido-14-hydroxy-17-(cyclopropylmethyl)nordesmorphine (17a)

The general method of compound 14a was used: α-N-Methylnaltrexamine (30 mg, 0.08 mmol), p-chlorobenzoic acid (20.4 mg, 0.13 mmol) and BOP (56 mg, 0.13 mmol) were combined in CH$_2$Cl$_2$ (2 mL). The product was purified by SiO$_2$ chromatography (20:1 CH$_2$Cl$_2$/MeOH) to provide 17 mg, 41% of the target compound as thick oil. R$_f$=0.08; ESI/MS: m/z=495 (MH$^+$), 493 (MH$^-$); $^1$H NMR (CDCl$_3$) δ 7.54-7.27 (m, 4H), 6.71 (d, J=8.1 Hz, 1H), 6.54 (d, J=8.1 Hz, 1H), 5.12-5.04 (m, 2H), 3.3-1.25 (m, 18H), 0.88 (m, 1H), 0.54 (m, 2H), 0.09 (m, 2H).

Example 39

6-α-(4'-Chloro)-N-methylbenzamido-14-hydroxy-17-(cyclopropylmethyl)nordesmorphine oxalate (17a—Oxalate)

The amide product 17a was converted to its oxalic salt using one equivalent of oxalic acid dihydrate in methanol. Solubility: 10 mg/mL in H$_2$O.

Example 40

6-β-(4'-Chloro)-N-methylbenzamido-14-hydroxy-17-(cyclopropylmethyl)nordesmorphine (17b)

The general method of compound 13a was used: β-N-Methylnaltrexamine (35 mg, 0.1 mmol), p-chlorobenzoic acid (23 mg, 0.15 mmol), BOP (66 mg, 0.15 mmol) and N—N-diisopropylethylamine (0.05 mL, 0.3 mmol) were combined in CH$_2$Cl$_2$ (2 mL). Basic hydrolysis with K$_2$CO$_3$ (0.2 g) and purification by SiO$_2$ chromatography (CH$_2$Cl$_2$/MeOH, 20:1, v:v) provided 29 mg, 59% of the target compound as a semi-solid. R$_f$=0.1; ESI/MS: m/z=495 (MH$^+$), 493 (MH$^-$); $^1$H NMR (CDCl$_3$) δ 7.38-7.21 (m, 4H), 6.62 (d, J=8.0 Hz, 1H), 6.46 (d, J=8.0 Hz, 1H), 4.7 (d, J=7.8 Hz, 1H), 3.11 (s, 3H), 3.06-1.52 (m, 14H), 0.82 (m, 1H), 0.53 (m, 2H), 0.11 (m, 2H).

Example 41

6-β-(4'-Chloro)-N-methylbenzamido-14-hydroxy-17-(cyclopropylmethyl)nordesmorphine oxalate (17b—Oxalate)

The amide product 17b was converted to its oxalic salt using one equivalent of oxalic acid dihydrate in methanol. Solubility: 6 mg/mL in H$_2$O.

Example 42

6-α-(3',4'-Dichloro)-N-methylbenzamido-14-hydroxy-17-(cyclopropylmethyl)nordesmorphine (18a)

The general method of compound 13a was used: 6-α-N-Methylnaltrexamine (30 mg, 0.08 mmol) was dissolved in CH$_2$Cl$_2$ (2 mL) and NEt$_3$ (0.03 mL, 0.25 mmol) and 3,4-dichlorobenzoyl chloride (42 mg, 0.20 mmol) was added. The product was purified by SiO$_2$ chromatography (CH$_2$Cl$_2$:MeOH, 20:1, v:v) to afford 29 mg, 65% as a white powder. R$_f$=0.07; ESI/MS m/z=529 (MH$^+$), 551 (MNa$^+$), 527 (MH$^-$), 565 (MCl$^-$); $^1$H NMR (CDCl$_3$) δ 7.42-7.33 (m, 3H), 6.72 (d, J=8.1 Hz, 1H), 6.53 (d, J=8.1 Hz, 1H), 5.11-5.07 (m, 2H), 3.35-1.25 (m, 18H), 0.88 (m, 1H), 0.53 (m, 2H), 0.09 (m, 2H).

Example 43

6-α-(3',4'-Dichloro)-N-methylbenzamido-14-hydroxy-17-(cyclopropylmethyl)nordesmorphine oxalate (18a—Oxalate)

The amide product 18a was converted to its oxalic salt using one equivalent of oxalic acid dihydrate in methanol. Solubility: 6.7 mg/mL in H$_2$O.

Example 44

6-β-(3',4'-Dichloro)-N-methylbenzamido-14-hydroxy-17-(cyclopropylmethyl)nordesmorphine (18b)

The general method of compound 13a was used: β-N-Methylnaltrexamine (50 mg, 0.14 mmol), 3,4-dichlorobenzoyl chloride (71 mg, 0.34 mmol) and NEt$_3$ (0.05 mL, 0.42 mmol) were combined in CH$_2$Cl$_2$ (2 mL). Basic hydrolysis with K$_2$CO$_3$ and purification of the crude product by SiO$_2$ chromatography (CH$_2$Cl$_2$:MeOH, 20:1, v:v) afforded 33 mg, 45% as a white powder. R$_f$=0.1; ESI/MS m/z=529 (MH$^+$), 551 (MNa$^+$), 527 (MH$^-$), 565 (MCl$^-$); $^1$H NMR (CDCl$_3$) δ 7.53-7.44 (m, 3H), 6.61 (d, J=7.6 Hz, 1H), 6.48 (d, J=7.6 Hz, 1H), 4.69 (d, J=7.3 Hz, 1H), 3.11 (s, 3H), 3.02-1.36 (m, 14H), 0.83 (m, 1H), 0.53 (m, 2H), 0.11 (m, 2H).

Example 45

6-β-(3',4'-Dichloro)-N-methylbenzamido-14-hydroxy-17-(cyclopropylmethyl)nordesmorphine oxalate (18b—Oxalate)

The amide product 18b was converted to its oxalic salt using one equivalent of oxalic acid dihydrate in methanol. Solubility: 16 mg/mL in H$_2$O.

Scheme 3. Synthesis of acrylamides

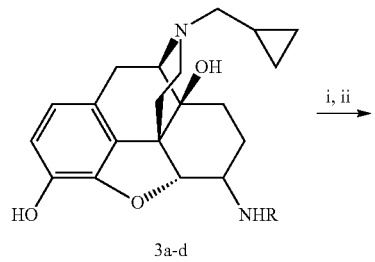

3a-d i, ii

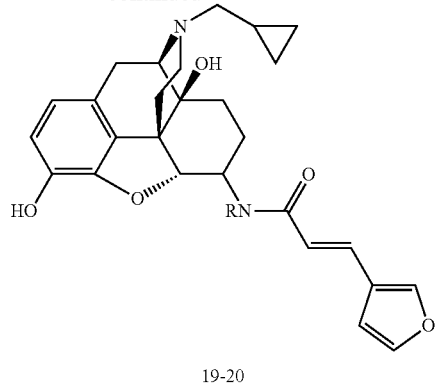

19-20
19a: R = H, 6-α
19b: R = H, 6-β
20a: R = CH$_3$, 6-α
20b: R = CH$_3$, 6-β i) 3-(3-Furyl)acrylic acid, BOP, DIEA, CH$_2$Cl$_2$;
ii) K$_2$CO$_3$, MeOH

Example 46

17-Cyclopropylmethyl-3,14β-dihydroxy-4,5α-epoxy-6α-trans-3-(3-furyl)acryl-amido]morphinan (19a)

The general method of compound 14a was used: 6-α-Naltrexamine, 3a (30 mg, 0.09 mmol), 3-(3-furyl)acrylic acid (18 mg, 0.13 mmol), BOP (58 mg, 0.13 mmol) and N,N-Diisopropylethylamine (0.05 mL, 0.26 mmol) were combined in anhydrous dichloromethane (2 mL) followed by base hydrolysis. The crude product was purified by flash chromatography (CH$_2$Cl$_2$/MeOH, 20:1, v:v) to give the target product 19a (26 mg, 64%). R$_f$=0.07; ESI/MS: m/z=464 (MH$^+$), 485 (MNa$^+$) 461 (MH$^-$), 497 (MCl$^-$); $^1$H NMR (CDCl$_3$) δ 7.59 (m, 1H), 7.49 (d, J=11 Hz, 1H), 7.37 (m, 1H), 6.74 (d, J=8.1 Hz, 1H), 6.54 (d, J=8.1 Hz, 1H), 6.49 (m, 1H), 6.15 (m, 1H), 4.71 (d, J=3.2 Hz, 1H), 3.12-0.84 (m, 15H), 0.53 (m, 2H), 0.12 (m, 2H); $^{13}$C NMR (CDCl$_3$) δ 165.7, 145.5, 144.3, 144.1, 137.5, 131.4, 131.3, 126.4, 122.9, 120.9, 119.4, 117.4, 107.7, 90.7, 69.7, 62.3, 59.9, 47.4, 46.3, 43.4, 33.7, 29.4, 23.1, 21.3, 9.6, 4.2.

Example 47

17-Cyclopropylmethyl-3,14β-dihydroxy-4,5α-epoxy-6α-trans-3-(3-furyl)acrylamido]morphinan oxalate (19a—Oxalate)

Compound 19a was converted to its oxalic salt using one equivalent of oxalic acid dihydrate in methanol. Solubility: 13.3 mg/mL in H$_2$O.

Example 48

17-Cyclopropylmethyl-3,14β-dihydroxy-4,5α-epoxy-6β-[-trans-3-(3-furyl)acrylamido]morphinan (19b)

The general method of compound 14a was used. 6-β-Naltrexamine (100 mg, 0.29 mmol), 3-(3-furyl)acrylic acid (60 mg, 0.44 mmol), BOP (195 mg, 0.44 mmol) and N,N-Diisopropylethylamine (0.15 mL, 0.88 mmol) was combined in anhydrous dichloromethane (3 mL) followed by base hydrolysis. The crude product was then purified by flash chromatography (CH$_2$Cl$_2$/MeOH, 20:1, v:v) to give the target product 19b (119 mg, 88%). R$_f$=0.04; ESI/MS: m/z=463 (MH$^+$), 485 (MNa$^+$) 461 (MH$^-$), 497 (MCl$^-$); $^1$H NMR (CDCl$_3$) δ 7.60 (m, 1H), 7.48 (d, J=15.5 Hz, 1H), 7.40 (m, 1H), 6.74 (d, J=8.1 Hz, 1H), 6.56-6.54 (m, J=8.1 Hz, 2H), 6.16 (d, J=15.5 Hz, 1H), 4.47 (d, J=7.5 Hz, 1H), 4.06 (m, 1H) 3.04-0.86 (m, 14H), 0.54 (m, 2H), 0.14 (m, 2H).

Example 49

17-Cyclopropylmethyl-3,14β-dihydroxy-4,5α-epoxy-6β-[-trans-3-(3-furyl)acrylamido]morphinan oxalate (19b.Oxalate)

Compound 19b was converted to its oxalic salt using one equivalent of oxalic acid dihydrate in methanol. Solubility: 24.0 mg/mL in H$_2$O.

Example 50

17-Cyclopropylmethyl-3,14β-dihydroxy-4,5α-epoxy-6α-[N-methyl-trans-3-(3-furyl)acrylamido]morphinan (20a)

The general method of compound 14a was used. A mixture of 6-α-N-methylnaltrexamine (20 mg, 0.06 mmol), 3-(3-furyl)acrylic acid (12 mg, 0.08 mmol), BOP (39 mg, 0.08 mmol) and N,N-Diisopropylethylamine (0.03 mL, 0.18 mmol) was combined in anhydrous dichloromethane (2 mL) followed by base hydrolysis. The crude product was then purified by flash chromatography (CH$_2$Cl$_2$/MeOH, 20:1, v:v) to give the target product 20a (25 mg, 87%). R$_f$=0.05; ESI/MS: m/z=477 (MH$^+$), 499 (MNa$^+$) 475 (MH$^-$); $^1$H NMR (CDCl$_3$) δ 7.63-7.56 (m, 2H), 7.40 (m, 1H), 6.72 (d, J=7.7 Hz, 1H), 6.67-6.60 (m, 2H), 6.53 (d, J=7.7 Hz, 1H), 5.15 (m, 1H), 4.92 (d, J=3.2 Hz, 1H), 3.63 (m, 1H), 3.10 (s, 3H), 3.04-1.54 (m, 13H), 0.86 (m, 1H), 0.53 (m, 2H), 0.12 (m, 2H).

Example 51

17-Cyclopropylmethyl-3,14β-dihydroxy-4,5α-epoxy-6α-[N-methyl-trans-3-(3-furyl)acrylamido]morphinan oxalate (20a—Oxalate)

Compound 20a was converted to its oxalic salt using one equivalent of oxalic acid dihydrate in methanol. Solubility: 16.0 mg/mL in H$_2$O.

Example 52

17-Cyclopropylmethyl-3,14β-dihydroxy-4,5α-epoxy-6β-[N-methyl-trans-3-(3-furyl)acrylamido]morphinan 20b The general method of compound 14a was used. 6-β-N-Methylnaltrexamine (26 mg, 0.07 mmol), 3-(3-furyl)acrylic acid (15 mg, 0.11 mmol), BOP (48 mg, 0.11 mmol) and N,N-Diisopropylethylamine (0.04 mL, 0.22 mmol) was combined in anhydrous dichloromethane (1.5 mL) followed by base hydrolysis. The crude product was then purified by flash chromatography (CH$_2$Cl$_2$/MeOH, 20:1, v:v) to give the target product 20b (33 mg, 95%). R$_f$=0.04; ESI/MS: m/z=477 (MH$^+$), 499 (MNa$^+$), 475 (MH$^-$), 511 (MCl$^-$); $^1$H NMR (CDCl$_3$) δ 7.51 (m, 1H), 7.46 (d, J=15.2 Hz, 1H), 7.36 (m, 1H), 6.83 (d, J=8.1 Hz, 1H), 6.64 (d, J=8.1 Hz, 1H), 6.59 (m, 1H), 6.34 (d, J=15.2 Hz, 1H), 4.59 (d, J=7.8 Hz, 1H), 3.75 (m, 1H), 3.11 (m, 2H), 3.03 (s, 3H), 2.79-1.44 (m, 11H), 0.85 (m, 1H), 0.54 (m, 2H), 0.14 (m, 2H).

Example 53

17-Cyclopropylmethyl-3,14β-dihydroxy-4,5α-epoxy-6β-[N-methyl-trans-3-(3-furyl)acrylamido]morphinan oxalate (20b-oxalate)

Compound 20b was converted to its oxalic salt using one equivalent of oxalic acid dihydrate in methanol. Solubility: 32.0 mg/mL in H$_2$O.

Scheme 4. Synthesis of Naltrexamide N-Oxides

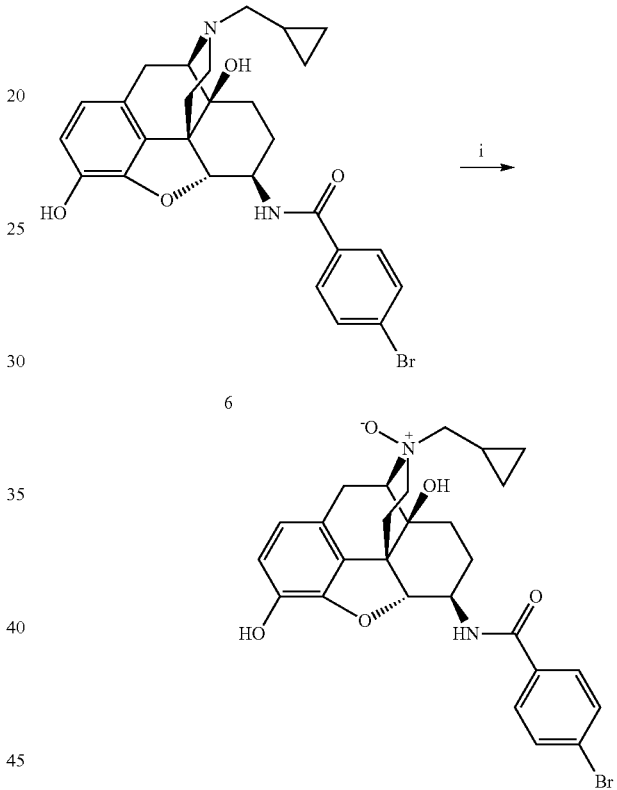

i) m-CPBA, CH$_2$Cl$_2$.

Example 54

General Procedure for the Synthesis of N-Oxides: 6-β-(4'-Bromo)benzamido-14-hydroxy-17-N,N-(cyclopropylmethyl)oxynordesmorphine (63)

The naltrexamide 6 (10 mg, 0.02 mmol) was dissolved in anhydrous dichloromethane (0.3 mL) and the solution was cooled to 0° C. To this solution, m-CPBA (4 mg, 0.02 mmol) was added and the mixture was stirred at room temperature for 12 h. Solvent was removed and the resulting white solid was purified by PTLC (CH$_2$Cl$_2$/MeOH, 20:1, v:v) to give 6 mg, 59% yield of the product as a white solid. R$_f$=0.2; ESI/MS: m/z=541 (MH$^+$); $^1$H NMR (CD$_3$OD) δ 7.76 (m, 2H), 7.64 (m, 2H), 7.36 (m, 1H), 6.72 (d, J=8.1 Hz, 1H), 6.67 (d, J=8.1 Hz, 1H), 4.73 (d, J=7.5 Hz, 1H), 3.92 (m, 1H), 3.79 (m, 1H), 3.61 (m, 1H), 3.35-1.49 (m, 12H), 0.73 (m, 2H), 0.48 (m, 2H).

Example 55

Naltrexamide N-Oxides (21) to (66)

The following naltrexamide N-oxides were prepared using the general procedure of Example 54 and quantified by mass spectrometry. All compounds showed the desired molecular ions (MH+) and (M+Na+) adducts.

17-Cyclopropylmethyl-3,14β-dihydroxy-4,5α-epoxy-6β-[(4'-methyl)benzamido]morphinan-N-oxide, (21);
17-Cyclopropylmethyl-3,14β-dihydroxy-4,5α-epoxy-6β-[(4'-trifluoromethyl)benzamido]morphinan-N-oxide, (22);
17-Cyclopropylmethyl-3,14β-dihydroxy-4,5α-epoxy-6β-[(4'-tert-butyl)benzamido]morphinan-N-oxide, (23);
17-Cyclopropylmethyl-3,14β-dihydroxy-4,5α-epoxy-6β-[(4'-dimethylamino)benzamido]morphinan-N-oxide, (24);
17-Cyclopropylmethyl-3,14β-dihydroxy-4,5α-epoxy-6β-[(thiophen-2'-yl)acetamido]morphinan-N-oxide, (25);
17-Cyclopropylmethyl-3,14β-dihydroxy-4,5α-epoxy-6α-N-methyl[(4'-bromo)benzamido]morphinan-N-oxide, (26);
17-Cyclopropylmethyl-3,14β-dihydroxy-4,5α-epoxy-6β-N-methyl[(4'-tert-butyl)benzamido]morphinan-N-oxide, (27);
17-Cyclopropylmethyl-3,14β-dihydroxy-4,5α-epoxy-6β-N-methyl[(3',4'-dichloro)benzamido]morphinan-N-oxide, (28);
17-Cyclopropylmethyl-3,14β-dihydroxy-4,5α-epoxy-6β-[(3',4'-dimethoxy)benzamido]morphinan-N-oxide, (29);
17-Cyclopropylmethyl-3,14β-dihydroxy-4,5α-epoxy-6β-[(3'-methoxy)benzamido]morphinan-N-oxide, (30);
17-Cyclopropylmethyl-3,14β-dihydroxy-4,5α-epoxy-6β-[(2'-pyridyl)acetamido]morphinan-N-oxide, (31);
17-Cyclopropylmethyl-3,14β-dihydroxy-4,5α-epoxy-6β-(benzamido)morphinan-N-oxide, (32);
17-Cyclopropylmethyl-3,14β-dihydroxy-4,5α-epoxy-6β-(phenylacetamido)morphinan-N-oxide, (33);
17-Cyclopropylmethyl-3,14β-dihydroxy-4,5α-epoxy-6β-[(3'-hydroxy)benzamido]morphinan-N-oxide, (34);
17-Cyclopropylmethyl-3,14β-dihydroxy-4,5α-epoxy-6β-[(4'-chloro)benzamido]morphinan-N-oxide, (35);
17-Cyclopropylmethyl-3,14β-dihydroxy-4,5α-epoxy-6α-(6-acetamido-2,3,4,6-tetra-O-benzyl-D-pyranose)morphinan-N-oxide, (36);
17-Cyclopropylmethyl-3,14β-dihydroxy-4,5α-epoxy-6α-(benzamido)morphinan-N-oxide, (37);
17-Cyclopropylmethyl-3,14β-dihydroxy-4,5α-epoxy-6β-[(4'-carbomethoxy)benzamido]morphinan-N-oxide, (38);
17-Cyclopropylmethyl-3,14β-dihydroxy-4,5α-epoxy-6β-[(4'-methoxy)phenylacetamido]morphinan N-oxide, (39);
17-Cyclopropylmethyl-3,14β-dihydroxy-4,5α-epoxy-6β-[(4'-nitro)benzamido]morphinan-N-oxide, (40);
17-Cyclopropylmethyl-3,14β-dihydroxy-4,5α-epoxy-6α-[(3',4'-dimethoxy)benzamido]morphinan-N-oxide, (41);
17-Cyclopropylmethyl-3,14β-dihydroxy-4,5α-epoxy-6β-[(3'-methoxy)benzamido]morphinan-N-oxide, (42);
17-Cyclopropylmethyl-3,14β-dihydroxy-4,5α-epoxy-6β-[(3',4'-dichloro)benzamido]morphinan-N-oxide, (43);
17-Cyclopropylmethyl-3,14β-dihydroxy-4,5α-epoxy-6β-[N-methyl-trans-3-(3-furyl)acrylamido]morphinan-N-oxide, (44);
17-Cyclopropylmethyl-3,14-β-dihydroxy-4,5α-epoxy-6α-N-methyl-[(4'-trifluoromethyl)benzamido]morphinan-N-oxide, (45);
17-Cyclopropylmethyl-3,14β-dihydroxy-4,5α-epoxy-6α-N-methyl-[(4'-bromo)benzamido]morphinan-N-oxide, (46);
17-Cyclopropylmethyl-3,14-β-dihydroxy-4,5α-epoxy-6α-N-methyl-[(4'-iodo)benzamido]morphinan-N-oxide, (47);
17-Cyclopropylmethyl-3,14β-dihydroxy-4,5α-epoxy-6α-N-methyl-[(4'-tert-butyl)benzamido]benzamido]morphinan-N-oxide, (48);
17-Cyclopropylmethyl-3,14β-dihydroxy-4,5α-epoxy-6β-[(4'-carboxy)benzamido]morphinan-N-oxide, (49);
17-Cyclopropylmethyl-3,14-β-dihydroxy-4,5α-epoxy-6α-N-methyl-[(4'-chloro)benzamido]morphinan-N-oxide, (50);
17-Cyclopropylmethyl-3,14-β-dihydroxy-4,5α-epoxy-6α-N-methyl-(3',4'-dichloro)morphinan-N-oxide, (51);
17-Cyclopropylmethyl-3,14β-dihydroxy-4,5α-epoxy-6β-[(3'-(N''-hydroxycarbamimidoyl)benzamido]morphinan-N-oxide, (52);
17-Cyclopropylmethyl-3,14β-dihydroxy-4,5α-epoxy-6β-[(3' cyano)benzamido]morphinan-N-oxide, (53);
17-Cyclopropylmethyl-3,14-β-dihydroxy-4,5α-epoxy-6β-N-methyl-[(4'-iodo)benzamido]morphinan-N-oxide, (54);
17-Methyl-3,14β-dihydroxy-4,5α-epoxy-6β-[(4'-methyl)benzamido]morphinan-N-oxide, (55);
17-Cyclopropylmethyl-3,14β-dihydroxy-4,5α-epoxy-6β-[(3'-fluoro-4'-trifluoromethyl)benzamido]morphinan-N-oxide, (56);
17-Cyclopropylmethyl-3,14β-dihydroxy-4,5α-epoxy-6β-[(4'-methylsulfonyl)benzamido]morphinan-N-oxide, (58);
17-Cyclopropylmethyl-3,14β-dihydroxy-4,5α-epoxy-6β-[(4'-chloro-3'-fluoro)benzamido]morphinan-N-oxide, (59);
17-Cyclopropylmethyl-3,14-β-dihydroxy-4,5α-epoxy-6β-N-methyl-(4'-bromo)morphinan-N-oxide, (60);
17-Cyclopropylmethyl-3,14-β-dihydroxy-4,5α-epoxy-6β-N-methyl-(4'-trifluoromethyl)morphinan-N-oxide, (61);
17-Cyclopropylmethyl-3,14-β-dihydroxy-4,5α-epoxy-6β-N-methyl-(4'-iodo)morphinan-N-oxide, (62);
17-Cyclopropylmethyl-3,14β-dihydroxy-4,5α-epoxy-6β-[(4'-bromo)benzamido]morphinan-N-oxide, (63);
17-Cyclopropylmethyl-3,14-β-dihydroxy-4,5α-epoxy-6β-N-methyl-(4'-chloro)morphinan-N-oxide, (64);
17-Cyclopropylmethyl-3,14β-dihydroxy-4,5α-epoxy-6β-[(3'-methoxy)benzamido]morphinan-N-oxide, (65);
17-Cyclopropylmethyl-3,14β-dihydroxy-4,5α-epoxy-6β-[(4'-iodo)benzamido]morphinan-N-oxide, (66);

Example 56

General Procedures for Cell Culture

HEK293 cells stably transfected with FLAG-tagged mouse μ- and κ-opioid and human nociceptin receptors or hemaglutinin-tagged mouse δ-opioid receptors were confirmed with Fluorescence Activated Cell Sorter (FACS) analysis and confocal microscopic visualization of cells on coverslips stained with fluorescent antibodies (SF: M1 & Alexa IgG$_{2b}$; HA: HA$_{11}$ & Alexa IgG$_1$). Cells were cultured under 7% CO$_2$ in Dulbecco's modified Eagle's medium containing 10% fetal bovine serum in the presence of 0.4 mg/mL Zeocin (for μ- and δ-receptor cells), 0.5 mg/mL of Geneticin (for κ-receptor cells), or 0.2 mg/mL hygromycin (for NOP-receptor cells) to select for the presence of the transfected plasmid (pcDNA3.1Zeo and pcDNA3.1) that codes for both the opioid receptor and antibiotic resistance.

Example 57

General Procedure for Membrane Preparation

HEK293 cells expressing the μ-, δ-, κ- and nociceptin (NOP) receptors were grown in 10 cm dishes. When the cells were nearly 100% confluent, cells were washed twice with ice-cold phosphate buffered saline and scraped from the dishes with a HME lysis buffer (pH 7.5; 100 mM HEPES, 8 mM $MgCl_2$, 4 mM EDTA, 10 mg/mL saponin and one mammalian protease inhibitor tablet). The cells were pelleted (14000 rpm, 15 min, 4° C.) and resuspended in HME buffer. Following a rapid freeze ($N_2$)/thaw cycle, the cells were sonicated on ice, repelleted and resuspended in HME buffer and stored at −80° C. until used. Protein concentrations of membrane samples were determined by visible spectophotometry (595 nm) using the BIORAD protein assay reagent and found to be 5.8 μg/μL (μ), 7.3 μg/μL (δ), 8.6 μg/μL (κ) and 3.5 μg/μL (NOP).

Example 58

General Procedure for [35S]GTPγS Binding Assay

Triplicate assays were done in 96-well plates on ice with each reaction containing [$^{35}$S]GTPγS (50 μM), cell membrane (10 μg protein), GDP (5 μM), and SPA beads (0.5 mg) with assay buffer (pH 7.5; 50 mM HEPES, 100 mM NaCl, 5 mM $MgCl_2$, mg/mL saponin) and the opioid ligands as before. Non-specific binding was determined in the presence of GTPγS (10 μM). Single drug dose-response curves (0.1 nM-10 μM) of [$^{35}$S]GTPγS stimulated binding were done at each opioid receptor with each compound and compared to the standard opioid agonist compounds 11, 14, 16 and 15 for the μ-, δ-, κ- and nociceptin receptors, respectively. Inhibition of opioid agonist-stimulated [$^{35}$S]-GTPγS binding of selective opioid agonists 11 (1 μM), 14 (200 nM), (−) 16 (2 μM) and 15 (1 μM) for the μ-, δ-, κ- and nociceptin receptors, respectively, were done in the presence of varying concentrations (10 pM-10 μM) of each compound. Membranes and GDP were incubated with the antagonists for 30 min, before the opioid agonists, [$^{35}$S]GTPγS and SPA beads were added. Assay plates were shaken for 45 min at 25° C., and then centrifuged (1500 rpm, 5 min, 25° C.) before [$^{35}$S]GTPγS-stimulated binding was assessed using the NXT TOP-COUNTER.

Example 59

Rat and Mouse Liver Microsome and Human Liver S-9 Stability Assays

A typical assay mixture contained rat or mouse liver microsomes or human liver S-9 (0.4-0.5 mg of protein), 100 μM potassium phosphate buffer (pH 7.4), 40 μM test compound, an NADPH-generating system consisting of 0.5 mM NADP$^+$, 0.5 mM glucose-6-phosphate, 5 IU/mL glucose-6-phosphate dehydrogenase, 1 mg/mL DETAPAC and 7 mM $MgCl_2$ for a final incubation volume of 0.1 mL[23]. Incubations were run for 0, 10, 25, 40 and 60 min in air with shaking at 37° C. in a water bath and were terminated by the addition of 1 mL $CH_2Cl_2$:2-propanol (3:1, v:v). After centrifugation at 13,000 rpm for 5 min, the organic fraction was collected and the solvent was removed with a stream of argon. The residue was reconstituted in methanol (200 L), centrifuged at 13,000 rpm for 5 min and the supernatant was analyzed by high-performance liquid chromatography with an Axxi-chrom (straight-phase) silica column (4.6 mm×250 mm, 5 m) or with a Supelco (reverse-phase) HS F5 pentafluorophenyl column (4.6 mm×250 mm, 5 m) as described above. Standard conditions utilized an isocratic, ternary-solvent system consisting of solvents A (methanol), B (isopropanol) and C (aqueous 70% $HClO_4$) set at a flow rate of 1.5 mL/min (straight-phase), or A, D (water) and E ($HCO_2H$) set at a flow rate of 1.0 mL/min (reverse-phase), =254 nm with retention times ($t_R$) evaluated in min.

Example 60

CYP Inhibition Assays

CYP Inhibition Assays.

To measure CYP3A4 activity, testosterone 6-hydroxylation, was determined by an HPLC method. To measure CYP2C9, diclofenac hydroxylase activity was measured by an HPLC method. For determination of CYP2B6, CYP2C19 and CYP2D6 activity, isozyme specific Vivid Blue substrate O-dealkylation was determined via a modified Panvera Vivid Assay Protocol. Briefly, for CYP2B6, 2C19 and 2D6, microsomes containing 1 pmol of CYP was added to 0.05 mM Tris buffer (pH 7.4) containing an NADPH generating system (i.e., 0.5 mM NADP$^+$, 0.5 mM glucose-6-phosphate dehydrogenase, 1 mg/mL DETAPAC, and 7 mM $MgCl_2$) in a total volume of 100 μL. Test compounds (10 μM) were added and the substrate (5 μM PanVera Vivid Assay substrate) was added to initiate the incubation after a brief but thorough mixing. Incubations were run in a 96-well plate (BD Falcon Microtest, Black Flat Bottom) for up to 60 min and monitored continuously to follow the linear portion of the fluorescent product versus time profile using a Wallac Victor$^2$ Multilabel Counter. The inhibition of amount of product formed was determined by interpolation from a standard curve and a comparison of the complete system without inhibitor. The average percent inhibition ±standard deviation was calculated from three separate experiments.

Example 61

Metabolism Studies of Compound 6

As a representative example, metabolic incubations were done with 6 in the presence of human or rat liver microsomes or highly purified human FMO3. The incubation mixture contained the NADPH-generating system as described above, 1 mg/mL DETAPAC and 7 mM $MgCl_2$, 0.4 mg of microsomes or 10 μg of human FMO3 in a total volume of 0.25 mL combined and mixed at 4° C. The incubation was initiated by the addition of 6 (30 μM) and placed in a 37° C. shaking incubator. At the appropriate time, the incubation was stopped by the addition of 2 volumes of ice cold acetonitrile (for the radiometric assay) and an aliquot was directly placed on an LK5DF preabsorbent TLC plates (Whatman, Maidstone, UK) using an eluant of EtAOc/MeOH/NH$_4$OH, 20/5/0.2, v/v) that separated compound 6,6-N-oxide and bromobenzoic acid with R$_f$ values of 0.58, 0.28 and 0.11, respectively. For analysis, 50 μg of 6,6-N-oxide and bromobenzoic acid was used as TLC standards and the UV-vis bands corresponding to these regions were scraped and placed in scintillation vials for counting and quantification. For the HPLC assay, the incubation was stopped by the addition of isopropanol/$CH_2Cl_2$ (3/1, v/v), mixed thoroughly and the organic layer was separated by centrifugation. The organic extracts were evaporated to dryness, taken up in MeOH and the products were separated by HPLC (i.e., Supleco column (4.6 mm×25 cm, Silica, 5 um) with a mobile phase of $CH_3CN$/potassium phosphate buffer, 1/1, v/v, pH=3) that separated 3b, 6-N-oxide and 6, with retention volumes of 4.1, 8.4 and 9.2 mL, respectively) at 235 nm. The analytes were quantified on the basis of HPLC peak height.

Example 62

In Vivo Metabolism Studies with Compound 6

Animal studies in male Wistar rats (275-310 g) with jugular vein and femoral artery catheters were administered radiolabelled 6 oxalate (100 µg/kg i.v. and 400 µg/kg, oral). For plasma analysis, blood was obtained from the catheters at various time points up to 8 h and centrifuged at 4° C. An aliquot of plasma was counted by scintillation counting. Brain distribution of radiolabeled 6 oxalate was also investigated in male Wistar rats administered 400 µg/kg by the oral route of administration. After 90 min post dosing, animals were anesthetized by i.p. ketamine/xylazine and blood samples were obtained by cardiac puncture. Brain tissues were immediately removed, weighed, homogenized with a mortar and pestle in borate buffer (pH 8.5)/acetonitrile, 1/1, v/v), centrifuged and an aliquot was measured by scintillation counting.

Example 63

General Procedure for Oral Ethanol and Saccharin Operant Self-Administration Training Ethanol or saccharin (SACC) self-administration training was conducted in standard operant cages (Coulbourn Instruments, PA) located in sound-attenuated, ventilated cubicles. Two 35-ml syringes dispensed either ethanol/SACC or water through plastic tubing into two stainless steel drinking cups mounted 4 cm above the grid floor and centered on the front panel of each chamber. Each drinking cup held 2 reinforcer deliveries (0.1 ml fluid/reinforcer). Two retractable levers were located 4.5 cm to either side of the drinking cups. Fluid delivery and recording of operant responses were controlled by a microcomputer. Briefly, animals were trained to voluntarily self-administer 10% (w/v) ethanol (n=10) or saccharin (n=6) by the oral route using the saccharin fadeout method[39] and were tested for their response for ethanol or saccharin solution in a two-lever free choice situation. Once baseline ethanol and saccharin intake were achieved (i.e., when responding across 3 consecutive days varied less than 20% and response rates correspond to pharmacologically relevant blood alcohol levels (BALs)), dose response testing for each compound commenced. To allow for a complete dissipation of any carry-over effects, a one week washout period, where rats were re-baselined during daily 30 min operant sessions, occurred between testing of each compound.

Example 64

Ethanol Self-Administration Analysis

Data were collected on-line simultaneously from multiple operant chambers. Results of the operant procedure are reported as mean cumulative number of bar presses for ethanol or saccharin. In general, tests for homogeneity of variance were first performed on the data. If the scores did not violate the assumption of homogeneity of variance, appropriate analyses of variance (ANOVA) were done. Data were analyzed using the StatView statistical package on a PC-compatible computer. Mixed-design ANOVAs were used with drug treatments as a within-subjects factor (i.e., repeated measures design for drug treatment). A priori analysis examining individual drug doses to vehicle control dose was conducted using paired t-tests. Significant drug effects were defined as having $p<0.05$ compared to vehicle-treated rats.

Example 65

Cocaine Self-Administration; Animals and Apparatus

Male Wistar rats (Charles River, Hollister, Calif.), each weighing between 300 g and 400 g at the time of testing opioid receptor ligands in the study, served as subjects. Rats were housed in groups of two or three in plastic cages with a reversed 12 h:12 h light/dark cycle with lights on at 8:00 PM. Food and water were available ad libitum. During experimental sessions, each rat was placed in an operant chamber (28× 26×20 cm; Med Associates Inc., St Albans, Vt.). The chamber had two retractable response levers mounted on a sidewall, and a stimulus light was mounted above each lever. A drug injection was delivered by a syringe pump (Razel™ Scientific Instruments, Georgia, Vt.) located on top of the cubicle. Experimental sessions were controlled and recorded by a PC computer with custom interface and software in the experimental room. Experimental sessions were conducted once a day during the dark (active) cycle. At the start of a session, two response levers were presented into the chamber, and responding on the right lever resulted in the delivery of 0.1 ml of a drug solution over 4 seconds. During an injection, a stimulus light above the active lever was illuminated and lasted throughout the time-out period (20 sec) that followed each injection. Pressing the left lever was counted but had no other programmed consequences. The session ended by the withdrawal of the levers.

Example 66

Cocaine Self-Administration Procedure

Detailed surgical methods were previously described (Wee et al. 2007). Briefly, rats were implanted with silastic catheters (0.3 mm ID×0.64 mm OD; Dow Corning Co. Midland, Mich.) into the right external jugular vein. After recovery from the surgery, rats were trained to self-administer 0.5 mg/kg/injection of cocaine in daily 1-hour sessions under a fixed-ratio (FR) 1 schedule for 10 days. Following these baseline sessions, rats were separated into two groups, balanced for cocaine self-administration in the last baseline session. The session length was kept to 1 hr for one group (short access, ShA, n=8) and was increased to 6 hrs for the other group (long access, LgA, n=8; escalation period). Sessions in this escalation period lasted for 15 days before testing the effect of opioid receptor ligands on cocaine self-administration. After 15 escalation sessions, the effect of SG-II-49 (Compound 6) on cocaine self-administration was tested under an FR1 schedule first and then under a progressive-ratio (PR) schedule. Test sessions were separated by at least two escalation sessions (ShA rats, 1-hour session, LgA rats, 6-hour session), and the doses of SG-II-49 (6) were tested in a counter-balanced manner across rats

Example 67

Data Analysis

The data were expressed as the mean number of injections as well as the mean milligram per kilogram for each group of rats. The effect of access on cocaine self-administration per session as well as in the first hour of a session was examined over the initial 15 escalation sessions using a repeated measures two-way analysis of variance (ANOVA; access×daily session) with the Bonferroni post hoc test. After 15 cocaine self-administration sessions with extended access, an increase in cocaine self-administration under a PR schedule in LgA rats was examined in comparison with ShA rats using the Student's t test. The effect of SG-II-49 or naltrexone on cocaine self-administration was evaluated using a repeated measures two-way ANOVA (access×dose) with the Bonferroni post hoc test. Software used for data analysis was Prism 4.0 (GraphPad, San Diego, Calif.).

Example 68

Receptor Binding and Functional Experiments

Receptor binding studies were conducted on human opioid receptors transfected into Chinese hamster ovary (CHO) cells. The μ cell line was maintained in Ham's F-12 medium supplemented with 10% fetal bovine serum (FBS) and 400 μg/mL Geneticin (G418). The δ and the κ cell lines were maintained in Dulbecco's minimal essential medium (DMEM) supplemented with 10% FBS, 400 μg/mL G418, and 0.1% penicillin/streptomycin. All cell lines were grown to confluence and then harvested for membrane preparation. The membranes for functional assays were prepared in buffer A (20 mM HEPES, 10 mM $MgCl_2$, and 100 mM NaCl at pH 7.4), and the membranes for binding assays were prepared in 50 mM Tris buffer (pH 7.7). Cells were scraped from the plates and centrifuged at 500 g for 10 min. The cell pellet was homogenized in buffer with a polytron, centrifuged at 20000 g for 20 min, washed, recentrifuged, and finally resuspended at 3 mg of protein/mL in buffer to determine the protein content. The homogenate was then stored at −70° C. in 1 mL aliquots. Binding assays were conducted using [3H] DAMGO, [3H]C1-DPDPE, and [3H]U69,593 at the μ, δ, and κ receptors, respectively. The assay was performed in triplicate in a 96-well plate. Nonspecific binding was determined with 1.0 μM of the unlabeled counterpart of each radioligand. Cell membranes were incubated with the appropriate radioligand and test compound at 25° C. for 60 min. The incubation was terminated by rapid filtration through glass fiber filter paper on a Tomtec cell harvester. The filters were dried overnight and bagged with 10 mL scintillation cocktail before counting for 2 min on a Wallac Betaplate 1205 liquid scintillation counter. Full characterization of compounds included analysis of the data for $IC_{50}$ values and Hill coefficients using PRISM. $K_i$ values were calculated using the Cheng Prusoff transformation:

$$K_i = \frac{IC_{50}}{1 + L/K_d}$$

where L is the radioligand concentration and $K_d$ is the binding affinity of the radioligand, as determined previously by saturation analysis.

What is claimed is:

1. A compound of formula (I):

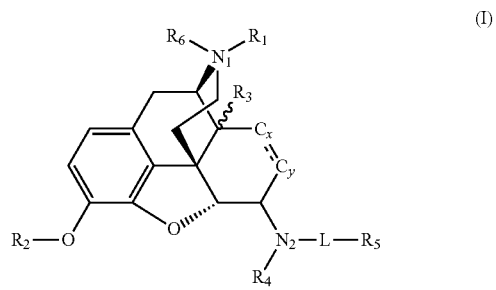

or a pharmaceutically acceptable salt thereof, wherein $R_1$ is selected from the group consisting of hydrogen, optionally substituted alkyl, optionally substituted alkenyl, optionally substituted alkynyl, optionally substituted cyclo alkyl, optionally substituted $(CH_2)_{1-5}$-cycloalkyl, optionally substituted cycloalkenyl, optionally substituted aryl, and optionally substituted heteroaryl;

$R_2$ is selected from the group consisting of hydrogen, optionally substituted alkyl, optionally substituted alkenyl, optionally substituted optionally substituted alkynyl, and optionally substituted akanoyl;

$R_3$ is selected from the group consisting of hydrogen, OH, and optionally substituted alkoxy;

$R_4$ is selected from the group consisting of hydrogen, optionally substituted alkyl, optionally substituted alkenyl, optionally substituted alkynyl, optionally substituted cycloalkyl, optionally substituted cycloalkenyl, optionally substituted aryl, and optionally substituted heteroaryl;

L is a group linking $N_2$ and $R_5$ and represents C=O;

$R_5$ is substituted aryl, wherein aryl is substituted with one or more alkyl, alkenyl, haloalkyl, hydroxyalkyl, heteroaryl, heterocycle, cycloalkyl, acylamino, trifluoromethyl, trifluoromethoxy, keto, thioxo, alkylthio, alkylsulfinyl, alkylsulfonyl, and cyano;

$R_6$ is selected from the group consisting of hydrogen, or $R_6$ is absent;

$N_1$ is a nitrogen atom, which is neutral when $R_6$ is absent, or is charged when $R_6$ is present, to satisfy the normal valence of a tertiary or quaternary nitrogen;

$N_2$ is a nitrogen atom, which is bound to the opiate nucleus in α or β stereochemistry or a mixture thereof; and $C_x$ and $C_y$ together form an alkylidene group (—$CH_2CH_2$—) or alkenylidene group (—CH=CH—); any of the attached hydrogens may be replaced to form a substituted alkenylidene group or substituted alkylidene of any possible stereochemistry.

2. The compound of claim 1 wherein:

$R_1$ is selected from the group consisting of hydrogen, $C_1$-$C_5$ optionally substituted alkyl, $C_2$-$C_5$ optionally substituted alkenyl, $C_2$-$C_5$ optionally substituted alkynyl, $C_3$-$C_6$ optionally substituted cycloalkyl, $C_3$-$C_6$ optionally substituted cycloalkenyl, $C_6$-$C_{12}$ optionally substituted aryl, and 5 or 6-membered optionally substituted heteroaryl containing 1-3 nitrogen, oxygen, or sulfur atoms, or a combination thereof;

$R_2$ is selected from the group consisting of hydrogen, $C_1$-$C_5$ optionally substituted alkyl, $C_2$-$C_5$ optionally substituted alkenyl, $C_2$-$C_5$ optionally substituted alkynyl, $C_3$-$C_6$ optionally substituted cycloalkyl, $C_3$-$C_6$ optionally substituted cycloalkenyl, $C_6$-$C_{12}$ optionally substituted aryl, 5 or 6-membered optionally substituted heteroaryl containing 1-3 nitrogen, oxygen, or sulfur atoms, or a combination thereof; and $C_2$-$C_6$ optionally substituted alkanoyl;

$R_3$ is selected from the group consisting of hydrogen, OH, and $C_1$-$C_6$ Alkoxy;

$R_4$ is selected from the group consisting of hydrogen, $C_1$-$C_5$ optionally substituted alkyl, $C_2$-$C_5$ optionally substituted alkenyl, $C_2$-$C_5$ optionally substituted alkynyl, $C_3$-$C_6$ optionally substituted cycloalkyl, $C_3$-$C_6$ optionally substituted cycloalkenyl, $C_6$-$C_{12}$ optionally substituted aryl, 5 or 6-membered optionally substituted heteroaryl containing 1-3 nitrogen, oxygen, or sulfur atoms, or a combination thereof; and $R_5$ is $C_6$-$C_{12}$ substituted aryl.

3. The compound of claim 1 wherein:

$R_1$ is selected from the group consisting of hydrogen, methyl, ethyl, isopropyl, 2-methyl-1-propyl, cyclopropymethyl, cyclobutylmethyl, allyl, 2-methyl-2-propenyl, 2-buten-1-yl, 3-methyl-2-buten-1-yl, 2,3-dimethyl-2-buten-1-yl, benzyl, Hydroxy-1'-methylalkyl, cyclohexenyl methyl; dihydrofuranyl methyl, and tetrahydrofuranylmethyl;

$R_2$ is selected from the group consisting of hydrogen, methyl, and acetyl $R_3$ is hydrogen or OH;

$R_4$ is hydrogen or methyl; and

L is C=O.

4. The compound of claim 1, wherein the compound is selected from the group consisting of:

6-β-(4'-methyl)benzamido-14-hydroxy-17-(cyclopropylmethyl)nordesmorphine;

6-β-(4'-methyl)benzamido-14-hydroxy-17-(cyclopropylmethyl)nordesmorphine-oxalate;

6-β-(4'-trifluoromethyl)benzamido-14-hydroxy-17-(cyclopropylmethyl)nordesmorphine;

6-β-(4'-trifluoromethyl)benzamido-14-hydroxy-17-(cyclopropylmethyl)nordesmorphine-oxalate;

6-(4'-t-butyl)benzamido-14-hydroxy-17-(cyclopropylmethyl)nordesmorphine;

6-β-(4'-t-butyl)benzamido-14-hydroxy-17-(cyclopropylmethyl)nordesmorphine-oxalate;

6-β-(3'-cyano)benzamido-14-hydroxy-17-(cyclopropylmethyl)nordesmorphine;

6-(3'-N-hydroxycarbamimidoyl)benzamido-14-hydroxy-17-(cyclopropylmethyl)-nordesmorphine;

6-α-(4'-trifluoromethyl)-N-methylbenzamido-14-hydroxy-17-(cyclopropylmethyl)nordesmorphine;

6-α-(4'-trifluoromethyl)-N-methylbenzamido-14-hydroxy-17-(cyclopropylmethyl) nordesmorphine oxalate;

6-α-(4'-trifluoromethyl)-N-methylbenzamido-14-hydroxy-17-(cyclopropylmethyl) nordesmorphine oxalate;

6-β-(4'-trifluoromethyl)-N-methylbenzamido-14-hydroxy-17-(cyclopropylmethyl) nordesmorphine;

6-β-(4'-trifluoromethyl)-N-methylbenzamido-14-hydroxy-17-(cyclopropylmethyl) nordesmorphine oxalate;

6-α-(4'-t-butyl)-N-methylbenzamido-14-hydroxy-17-(cyclopropylmethyl)nordesmorphine;

6-α-(4'-t-butyl)-N-methylbenzamido-14-hydroxy-17-(cyclopropylmethyl)nordesmorphine oxalate;

6-β-(4'-t-butyl)-N-methylbenzamido-14-hydroxy-17-(cyclopropylmethyl)nordesmorphine; and 6-β-(4'-t-butyl)-N-methylbenzamido-14-hydroxy-17-(cyclopropylmethyl)nordesmorphine oxalate.

5. A pharmaceutical composition comprising: a compound of claim 1; and a pharmaceutically acceptable excipient or earner.

6. A method of modulating the activity of an opioid receptor, comprising contacting the opioid receptor with a compound of claim 1, wherein the opioid receptor is selected from the group consisting of μ-opioid receptor, δ-opioid receptor, and κ-opioid receptor.

7. The method of claim 6, wherein the contacting is in a subject and the method further comprises, prior to the contacting, the step of identifying the subject in need of such contacting.

8. The method of claim 6, wherein the compound is an opioid receptor antagonist, an opioid receptor partial antagonist, an opioid receptor partial agonist, an opioid receptor inverse agonist, or an opioid receptor partial inverse agonist.

9. The method of claim 7, wherein the contacting comprises administering the compound of claim 1 to the subject.

10. The method of claim 7, wherein the contacting is in vitro.

11. The method of claim 7, wherein the subject suffers from alcohol addiction or cocaine addiction.

\* \* \* \* \*